United States Patent
Colvin, Jr.

(10) Patent No.: US 6,304,766 B1
(45) Date of Patent: Oct. 16, 2001

(54) OPTICAL-BASED SENSING DEVICES, ESPECIALLY FOR IN-SITU SENSING IN HUMANS

(75) Inventor: Arthur E. Colvin, Jr., Mt. Airy, MD (US)

(73) Assignee: Sensors for Medicine and Science, Germantown, MD (US)

(*) Notice: Subject to any disclaimer, the term of this patent is extended or adjusted under 35 U.S.C. 154(b) by 0 days.

(21) Appl. No.: 09/140,747

(22) Filed: Aug. 26, 1998

(51) Int. Cl.[7] .................................................. A61B 5/00
(52) U.S. Cl. ................................... 600/317; 128/903
(58) Field of Search ................................ 600/310, 316, 600/317, 322, 342, 343, 473, 476; 128/503

(56) References Cited

U.S. PATENT DOCUMENTS

| | | |
|---|---|---|
| 3,229,684 | 1/1966 | Nagumo et al. . |
| 3,576,554 | 4/1971 | Temps, Jr. et al. . |
| 3,612,866 | 10/1971 | Stevens .................................. 250/71 |
| 3,649,833 | 3/1972 | Leaf . |
| 3,800,300 | 3/1974 | Van Oosterhout . |
| 3,839,708 | 10/1974 | Bredesen et al. . |
| 3,853,117 | 12/1974 | Murr . |

(List continued on next page.)

FOREIGN PATENT DOCUMENTS

| | | |
|---|---|---|
| 4341903 | 6/1995 | (DE) . |
| 19826294 | 2/2000 | (DE) . |
| 0619101 | 12/1994 | (EP) . |
| 0646313 | 5/1995 | (EP) . |
| 693271 | 1/1996 | (EP) . |
| 2680672 | 5/1993 | (FR) . |
| 2258589 | 2/1993 | (GB) . |
| 8704900 | 8/1987 | (WO) . |
| 9207505 | 5/1992 | (WO) . |
| 9733513 | 9/1997 | (WO) . |
| 9966309 | 12/1999 | (WO) . |

OTHER PUBLICATIONS

\* "Mini–Portable Reader Standard and Extended Models" Hughes Identification Devices information pamphlet HS5105L Series (4 pages).
\* "Implantable Transponder" Trovan Electronic Identification Systems pamphlet, Model—ID 100. (2 pages).
\* "Hand Held Reader" Trovan electronic Identification Systems pamphlet, Model—LID 500. (2 pages).

(List continued on next page.)

Primary Examiner—Eric F. Winakur
(74) Attorney, Agent, or Firm—Rothwell, Figg, Ernst & Manbeck

(57) ABSTRACT

An optical-based sensor for detecting the presence or amount of an analyte. The sensor has a sensor body which functions as a wave guide, with a source of radiation embedded therein. Radiation emitted by the source interacts with indicator molecules on the surface of the body. At least one optical characteristics of the indicator molecules varies with analyte concentration. For example, the level of fluorescence of fluorescent indicator molecules or the amount of light absorbed by light-absorbing indicator molecules vary as a function of analyte concentration. Radiation (light) emitted or reflected by the indicator molecules enters and is internally reflected throughout the sensor body. A photosensitive element embedded within the sensor body generates a signal indicative of the level of internally reflected radiation and, hence, the concentration of the analyte. Preferred embodiments are totally self-contained and are sized and shaped for use in vivo in a human being. Such embodiments further include a power source, e.g. an inductor, which powers the source of radiation using external means, as well as a transmitter, e.g. an inductor, to transmit to external pickup means the signal representing the level of analyte.

95 Claims, 13 Drawing Sheets

U.S. PATENT DOCUMENTS

| | | | |
|---|---|---|---|
| 3,872,455 | 3/1975 | Fuller et al. | |
| 3,893,111 | 7/1975 | Cotter | |
| 3,949,388 | 4/1976 | Fuller | |
| 3,972,320 | 8/1976 | Kalman | |
| 4,041,954 | 8/1977 | Ohara | |
| 4,160,971 | 7/1979 | Jones et al. | |
| 4,186,749 | 2/1980 | Fryer | |
| 4,262,632 | 4/1981 | Hanton et al. | |
| 4,361,153 | 11/1982 | Slocum et al. | |
| 4,401,122 | 8/1983 | Clark, Jr. | |
| 4,531,526 | 7/1985 | Genest | |
| 4,677,008 | 6/1987 | Webb | 428/35 |
| 4,680,268 | 7/1987 | Clark, Jr. | |
| 4,703,756 | 11/1987 | Gough et al. | |
| 4,704,029 * | 11/1987 | Van Heuvelen | 600/316 |
| 4,730,188 | 3/1988 | Milheiser | |
| 4,737,464 | 4/1988 | McConnell et al. | |
| 4,746,830 | 5/1988 | Holland | |
| 4,752,115 | 6/1988 | Murray, Jr. et al. | |
| 4,755,667 | 7/1988 | Marsoner et al. | |
| 4,854,328 | 8/1989 | Pollack | |
| 4,863,470 | 9/1989 | Carter | |
| 4,875,483 | 10/1989 | Vollmann et al. | |
| 4,935,632 | 6/1990 | Hart | 250/486.1 |
| 4,992,794 | 2/1991 | Brouwers | |
| 5,010,893 | 4/1991 | Sholder | |
| 5,012,286 | 4/1991 | Kawano et al. | |
| 5,028,918 | 7/1991 | Giles et al. | |
| 5,036,869 | 8/1991 | Inahara | |
| 5,039,490 | 8/1991 | Marsoner et al. | |
| 5,041,826 | 8/1991 | Milheiser | |
| 5,084,699 | 1/1992 | DeMichele | |
| 5,095,309 | 3/1992 | Troyk et al. | |
| 5,157,262 | 10/1992 | Marsoner et al. | |
| 5,211,129 | 5/1993 | Taylor et al. | |
| 5,218,343 | 6/1993 | Stobbe et al. | |
| 5,235,326 | 8/1993 | Beigel et al. | |
| 5,281,825 | 1/1994 | Berndt et al. | 250/458.1 |
| 5,300,120 | 4/1994 | Knapp et al. | |
| 5,314,457 | 5/1994 | Jeutter et al. | |
| 5,342,789 | 8/1994 | Chick et al. | |
| 5,517,313 | 5/1996 | Colvin, Jr. | 356/417 |
| 5,628,310 | 5/1997 | Rao et al. | |
| 5,630,836 | 5/1997 | Prem et al. | |
| 5,674,288 | 10/1997 | Knapp et al. | |
| 5,682,149 | 10/1997 | Hofman | |
| 5,708,957 | 1/1998 | Chuang et al. | 422/82.07 |
| 5,725,578 | 3/1998 | Knapp et al. | |
| 5,735,887 | 4/1998 | Barreras, Sr. et al. | |
| 5,833,603 * | 11/1998 | Kovacs et al. | 600/317 |
| 5,855,609 | 1/1999 | Knapp | |
| 5,922,285 | 7/1999 | Melendez et al. | |
| 5,939,609 | 8/1999 | Knapp et al. | |
| 5,977,431 | 11/1999 | Knapp et al. | |
| 6,002,954 | 12/1999 | Van Antwerp et al. | |
| 6,011,984 | 1/2000 | Van Antwerp et al. | |

OTHER PUBLICATIONS

\* Wouters et al. "A Low Power Multi–Sensor Interface for Injectable Microprocessor–Based Animal Monitoring System" *Sensors and Acutuators A*, 41–42 (1994) 198–206.

\* "DIOG Database Guide (Standard Search Service)" SRS Information Technologies, 1987 (7 pages).

\* "Injectable Transponder Small Size" Hughes Identification Devices information pamphlet TX1400L (2 pages).

Brauker et al., "Neovascularization of synthetic membranes directed by membrane microarchitecture", *Journal of Biomedical Medical Research*, vol. 29, 1517–1524 (1995).

Chuang and Arnold,"Radioluminescent Light Source for Optical Oxygen Sensors", *Analytical Chemistry*, vol. 69, No. 10, 1899–1903, 1997.

Geller, et al., "Immunoisolation of Tumor Cells: Generation of Antitumor Immunity Through Indirect Presentation of Antigen", *Journal of Immunotherapy*, 20(2):131–137 (1997).

Geller, et al., "Use of An Immunoisolation Device for Cell Transplantation and Tumor Immunotherapy", pp. 1–23 w/attached Figures 1–7.

Shamlou et al, "Amphiphilic networks. X. Diffusion of glucose and insulin (and nondiffusion of albumin) through amphiphilic membranes", *Journal of Biomedical Materials Research*, vol. 35, 157–163 (1997).

Kennedy, "Tailoring polymers for biological uses" *Chemtech*, pp. 24–32, 1994.

Tuan, "Recombinant Protein Protocols, Detection and Isolation", *Methods in Molecular Biology*, vol. 63, pp. 373–387.

Ward, "Development of a Hybrid Artificial Pancreas with a Dense Polyurethane Membrane", *ASAIO Journal*, vol. 39, No. 3, pp. M261–M267.

Wilkins, "Biomaterials for Implanted Closed Loop Insulin Delivery System: A Review", *Biosensors and Bioelectronics* 5, pp. 167–203, 1990.

Advertisement pamphlet entitled "RFID: Everything you need to know" by Motorola Indala Corporation, 1996, 1997.

Pamphlet entitled "Divvying up the biostent market", *Bio-Century, The Bernstein Report on BioBusiness*, pp. A6, Aug. 10. 1998.

Advertising pamphlet entitled "Biocompatibility, controlled porosity, inertness, strength and comformability.", *Gore–Tex Medical Products*, 1990.

Product pamphlet for "Preclude Pericardial Membrane", *W.L. Gore & Associates, Inc.*, 1996.

Product pamphlet for "The Duraflo® Biocompatible Treatment", *Baxter Healthcare Corporation*, 1995.

"Laminin–5 inhibits human keratinocyte migration", *Exp Cell Res*, 2322:2 330–9, 1998 (abstract only).

\* cited by examiner

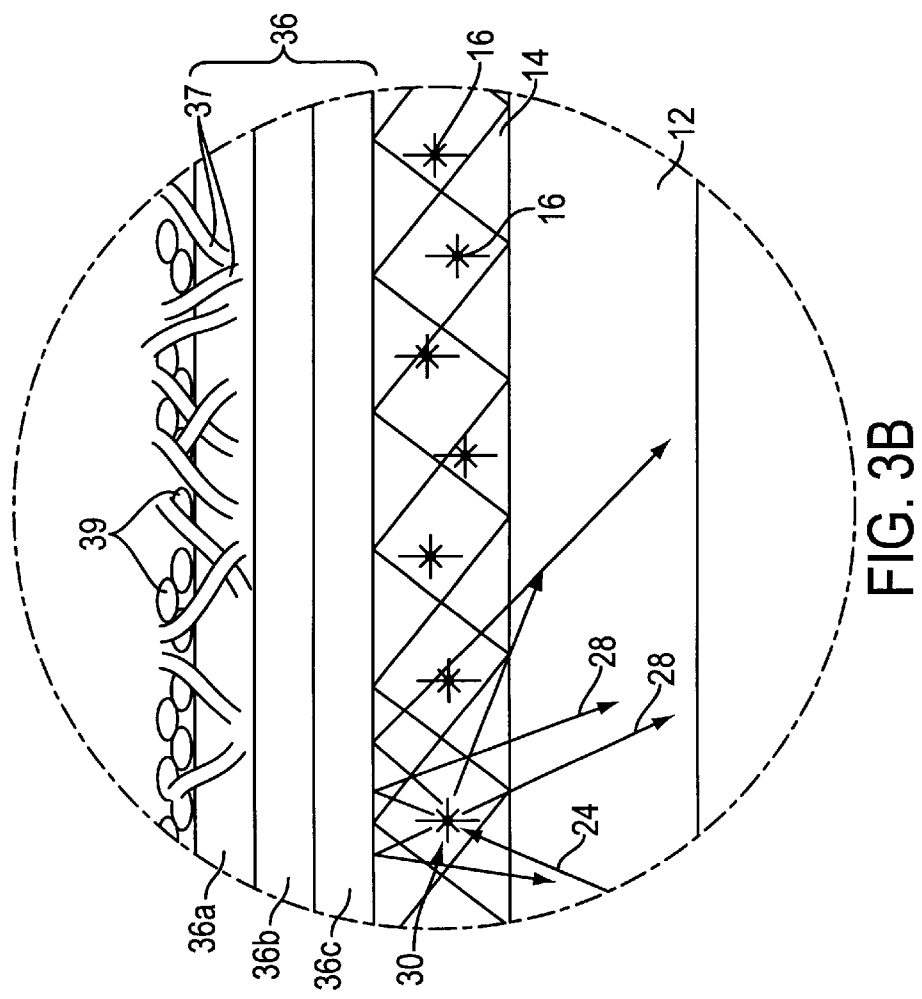
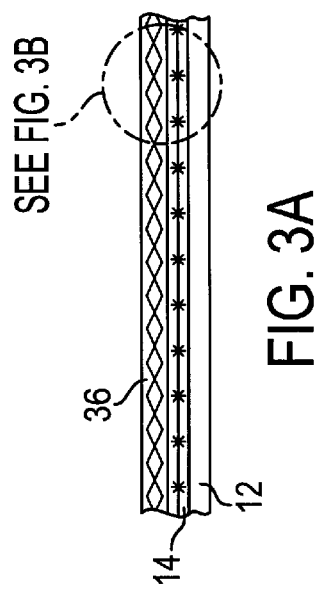

OPTICAL-BASED SENSING DEVICES, ESPECIALLY FOR IN-SITU SENSING IN HUMANS

BACKGROUND OF THE INVENTION

1. Field of Invention

The invention relates to electro-optical sensing devices for detecting the presence or concentration of an analyte in a liquid or gaseous medium. More particularly, the invention relates to (but is not in all cases necessarily limited to) optical-based sensing devices which are characterized by being totally self-contained, with a smooth and rounded oblong, oval, or elliptical shape (e.g., a bean- or pharmaceutical capsule-shape) and an extraordinarily compact size which permit the device to be implanted in humans for in-situ detection of various analytes.

2. Background Art

U.S. Pat. No. 5,356,417, the disclosure of which is incorporated herein by reference, describes a fluorescence-based sensing device comprising indicator molecules and a photosensitive element, e.g., a photodetector. Broadly speaking, in the context of the field of the present invention, indicator molecules are molecules one or more optical characteristics of which is or are affected by the local presence of an analyte. In the device according to U.S. Pat. No. 5,517,313, a light source, e.g., a light-emitting diode ("LED"), is located at least partially within a layer of material containing fluorescent indicator molecules or, alternatively, at least partially within a wave guide layer such that radiation (light) emitted by the source strikes and causes the indicator molecules to fluoresce. A high-pass filter allows fluorescent light emitted by the indicator molecules to reach the photosensitive element (photodetector) while filtering out scattered light from the light source.

The fluorescence of the indicator molecules employed in the device described in U.S. Pat. No. 5,517,313 is modulated, i.e., attenuated or enhanced, by the local presence of an analyte. For example, the orange-red fluorescence of the complex tris(4,7-diphenyl-1,10-phenanthroline) ruthenium(II) perchlorate is quenched by the local presence of oxygen. Therefore, this complex can be used advantageously as the indicator molecule in an oxygen sensor. Indicator molecules whose fluorescence properties are affected by various other analytes are known as well.

Furthermore, indicator molecules which absorb light, with the level of absorption being affected by the presence or concentration of an analyte, are also known. See, for example, U.S. Pat. No. 5,512,246, the disclosure of which is incorporated by reference, which discloses compositions whose spectral responses are attenuated by the local presence of polyhydroxyl compounds such as sugars. It is believed, however, that such light-absorbing indicator molecules have not been used before in a sensor construct like that taught in U.S. Pat. No. 5,517,313 or in a sensor construct as taught herein.

In the sensor described in U.S. Pat. No. 5,517,313, the material which contains the indicator molecules is permeable to the analyte. Thus, the analyte can diffuse into the material from the surrounding test medium, thereby affecting the fluorescence of the indicator molecules. The light source, indicator molecule-containing matrix material, high-pass filter, and photodetector are configured such that fluorescent light emitted by the indicator molecules impacts the photodetector such that an electrical signal is generated that is indicative of the concentration of the analyte in the surrounding medium.

The sensing device described in U.S. Pat. No. 5,517,313 represents a marked improvement over devices which constitute prior art with respect to U.S. Pat. No. 5,517,313. There has, however, remained a need for sensors that permit the detection of various analytes in an extremely important environment—the human body. Moreover, further refinements have been made in the field, which refinements have resulted in smaller and more efficient devices

SUMMARY OF THE INVENTION

In general, a sensor according to one aspect of the invention is totally self-contained, with a source of radiation (e.g., an LED) and a photosensitive element (e.g., a photodetector) both completely embedded within a light-transmitting sensor body that functions as a wave guide. Indicator molecules are located on the outer surface of the sensor body, e.g., directly coated thereon or immobilized within a polymer matrix layer. When the radiation source emits radiation, a substantial portion of the radiation is reflected within the sensor body due to internal reflection from the interface of the sensor body and the surrounding medium (polymer matrix or medium in which the analyte is present). When the radiation impacts the interface of the sensor body and the surrounding medium, it interacts with the indicator molecules immobilized on the surface of the sensor body. Radiation emitted by the indicator molecules (i.e., fluorescent light in the case of fluorescent indicator molecules) or emitted by the source and not absorbed by the indicator molecules (e.g., in the case of light-absorbing indicator molecules) is reflected throughout the sensor body due to internal reflection. The internally reflected radiation strikes the photosensitive element such that a signal is generated that is indicative of the presence and/or concentration of the analyte.

A sensor according to this aspect of the invention is constructed with components that permit the source of radiation to be powered either by external means, e.g., an electromagnetic wave, ultrasound, or infrared light, or by wholly internal means, e.g., by using radioluminescence or components such as microbatteries, microgenerators, piezoelectrics, etc. The sensor also has components to transmit a signal indicative of the level of internally reflected light or other radiation, from which level of internally reflected radiation the analyte concentration is determined. Such components may be an inductor that is separate from a power-receiving inductor, or the same inductor might be used both to receive power-generating electromagnetic energy and to transmit information-bearing electromagnetic signal waves.

According to another aspect of the invention, a sensor is constructed to facilitate its use subcutaneously in a living human being. To that end, according to this aspect of the invention, a sensor is approximately the size and shape of a bean or pharmaceutical cold capsule. Furthermore, the sensor preferably is provided with a sensor/tissue interface layer which either prevents the formation of scar tissue or which overcomes the formation of scar tissue by promoting the ingrowth of analyte-carrying vascularization. The shape of a sensor according to this aspect of the invention has been found in and of itself to provide beneficial optical properties, and therefore such a sensor could be constructed for applications other than in the human body, i.e., without an interface layer and/or with electrical leads extending into and out of the sensor.

A sensor according to another aspect of the invention is constructed with light-absorbing (or other radiation-absorbing) indicator molecules which absorb the radiation generated by the source. The level of absorption varies as a function of the analyte concentration. By measuring the amount of internally reflected radiation, the analyte concentration can be determined.

A sensor according to another aspect of the invention capitalizes on the relationship between the density of a medium and its refractive index to measure analyte concentration. As analyte concentration varies, the density of the medium to which the sensor is exposed changes, and therefore the refractive index of the surrounding medium changes as well. As the refractive index of the surrounding medium changes, the amount of light that is reflected internally (or, conversely, which passes across the sensor/medium interface) also changes, and this change in illumination can be measured by a photosensitive element within the sensor and correlated with the locally surrounding analyte concentration.

BRIEF DESCRIPTION OF THE DRAWINGS

These and other aspects of the invention will be apparent from the detailed description of the invention and the following figures, in which:

FIG. 3 is a detail view of the circled portion of FIG. 1 demonstrating internal reflection within the body of the sensor and a preferred construction of the sensor/tissue interface layer;

DETAILED DESCRIPTION OF THE INVENTION

Figure 1:
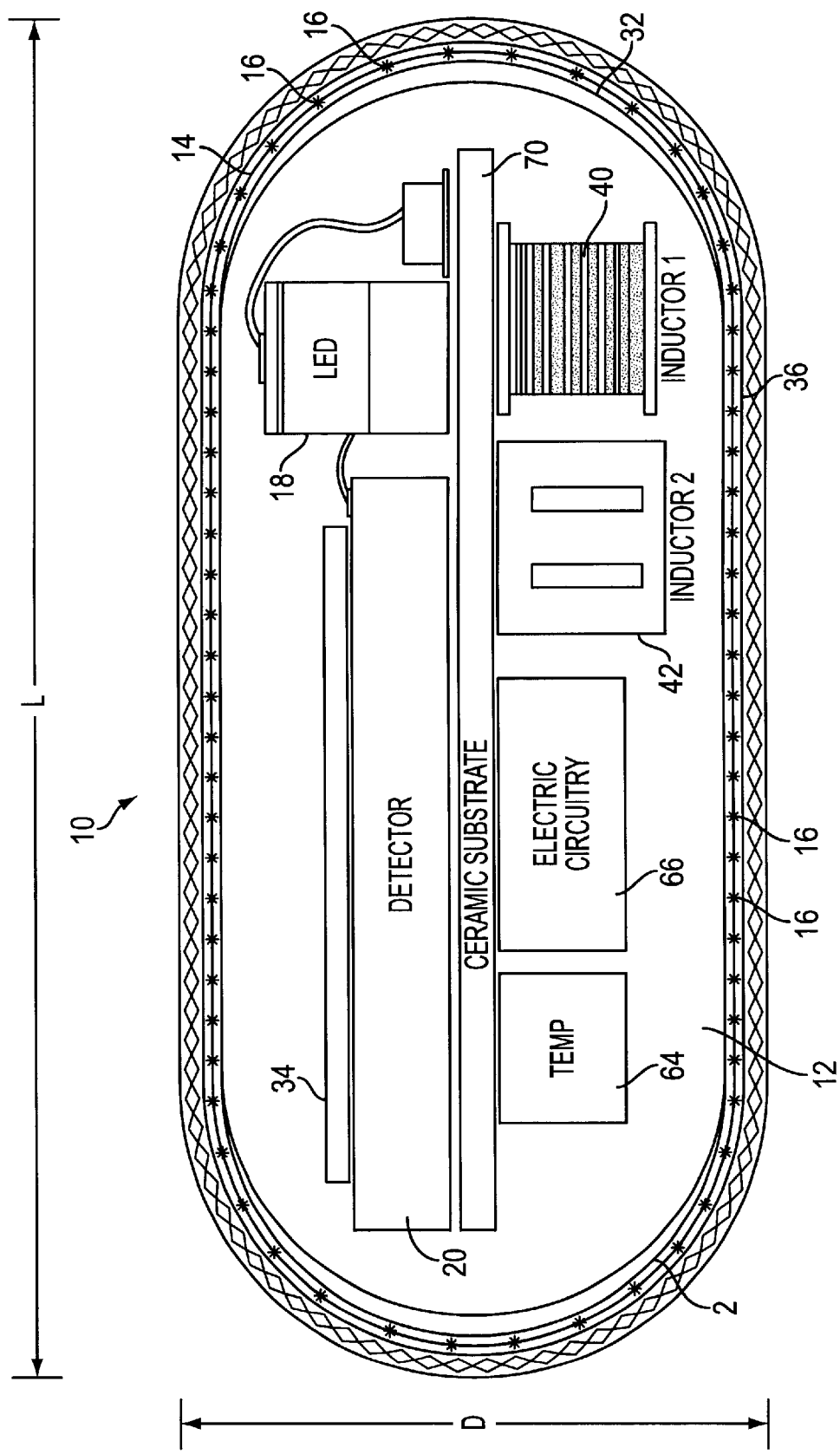
FIG. 1 is a schematic, section view of a fluorescence-based sensor according to the invention.

An optical-based sensor ("sensor") 10 according to one aspect of the invention, which operates based on the fluorescence of fluorescent indicator molecules, is shown in FIG. 1. The sensor 10 has as its primary components a sensor body 12; a matrix layer 14 coated over the exterior surface of the sensor body 12, with fluorescent indicator molecules 16 distributed throughout the layer; a radiation source 18, e.g. an LED, that emits radiation, including radiation over a range of wavelengths which interact with the indicator molecules (referred to herein simply as "radiation at a wavelength which interacts with the indicator molecules"), i.e., in the case of a fluorescence-based sensor, a wavelength which causes the indicator molecules 16 to fluoresce; and a photosensitive element 20, e.g. a photodetector, which, in the case of a fluorescence-based sensor, is sensitive to fluorescent light emitted by the indicator molecules 16 such that a signal is generated in response thereto that is indicative of the level of fluorescence of the indicator molecules. In the simplest embodiments, indicator molecules 16 could simply be coated on the surface of the sensor body. In preferred embodiments, however, the indicator molecules are contained within the matrix layer 14, which comprises a biocompatible polymer matrix that is prepared according to methods known in the art and coated on the surface of the sensor body as explained below. Suitable biocompatible matrix materials, which must be permeable to the analyte, include polymethacyclate and hydrogels which, advantageously, can be made selectively permeable—particularly to the analyte—i.e., they perform a molecular weight cut-off function.

Figure 2:
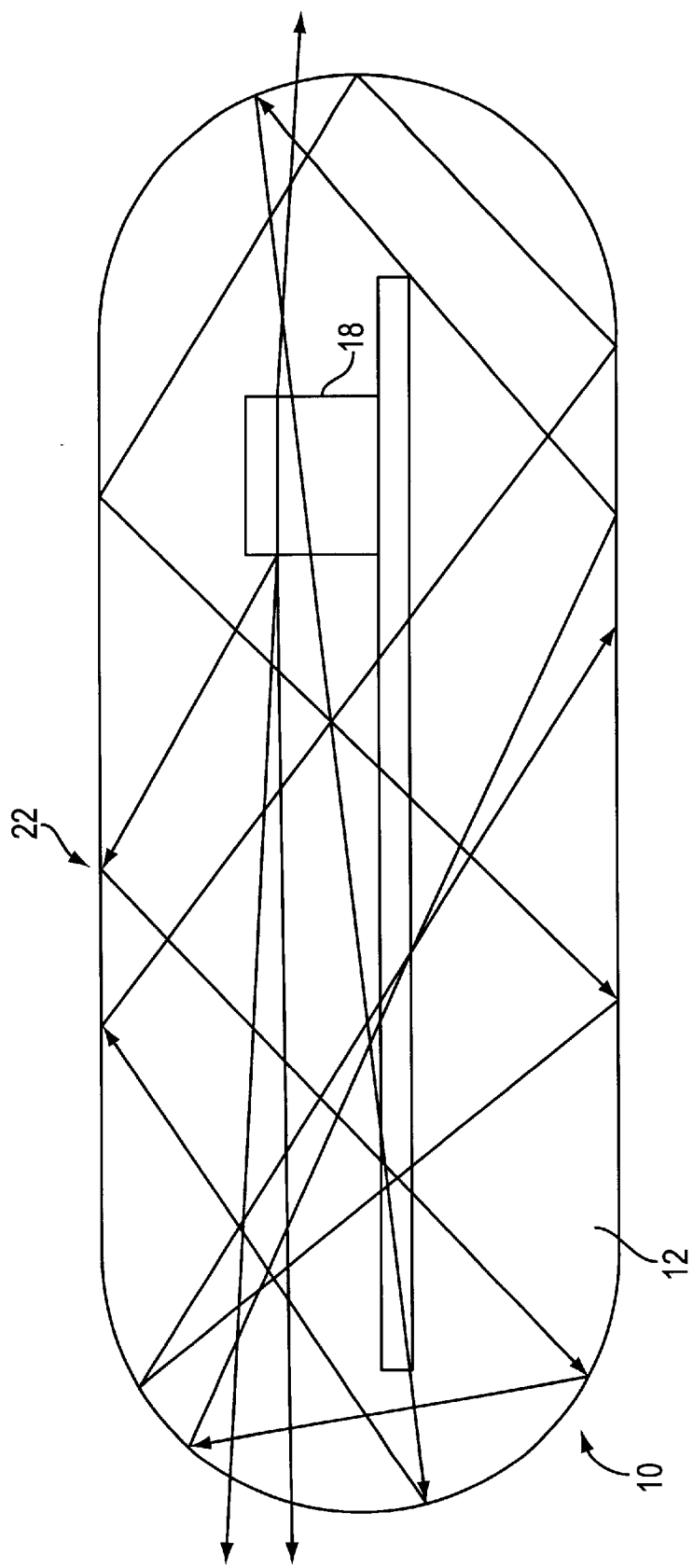
FIG. 2 is a schematic diagram of the fluorescence-based sensor shown in FIG. 1 illustrating the wave guide properties of the sensor.

The sensor 12 advantageously is formed from a suitable, optically transmissive polymer material which has a refractive index sufficiently different from that of the medium in which the sensor will be used such that the polymer will act as an optical wave guide. Preferred materials are acrylic polymers such as polymethylmethacrylate, polyhydroxypropylmethacrylate and the like, and polycarbonates such as those sold under the trademark Lexan®. The material allows radiation employed by the device—radiation generated by the radiation source 18 (e.g., light at an appropriate wavelength in embodiments in which the radiation source is an LED) and, in the case of a fluorescence-based embodiment, fluorescent light emitted by the indicator molecules—to travel through it. As shown in FIG. 2, radiation (e.g., light) is emitted by the radiation source 18 and (at least some) is reflected internally at the surface of the sensor body 12, e.g., as at location 22, thereby "bouncing" back-and-forth throughout the interior of the sensor body 12.

It has been found that light reflected from the interface of the sensor body and the surrounding medium is capable of interacting with indicator molecules coated on the surface (whether coated directly thereon or contained within a matrix), e.g., exciting fluorescence in fluorescent indicator molecules coated on the surface. In addition, light which strikes the interface at angles, measured relative to a normal to the interface, too small to be reflected passes through the interface and also excites fluorescence in fluorescent indicator molecules. Other modes of interaction between the light (or other radiation) and the interface and the indicator molecules have also been found to be useful depending on the construction of and application for the sensor. Such other modes include evanescent excitation and surface plasmon resonance type excitation.

Figure 4:
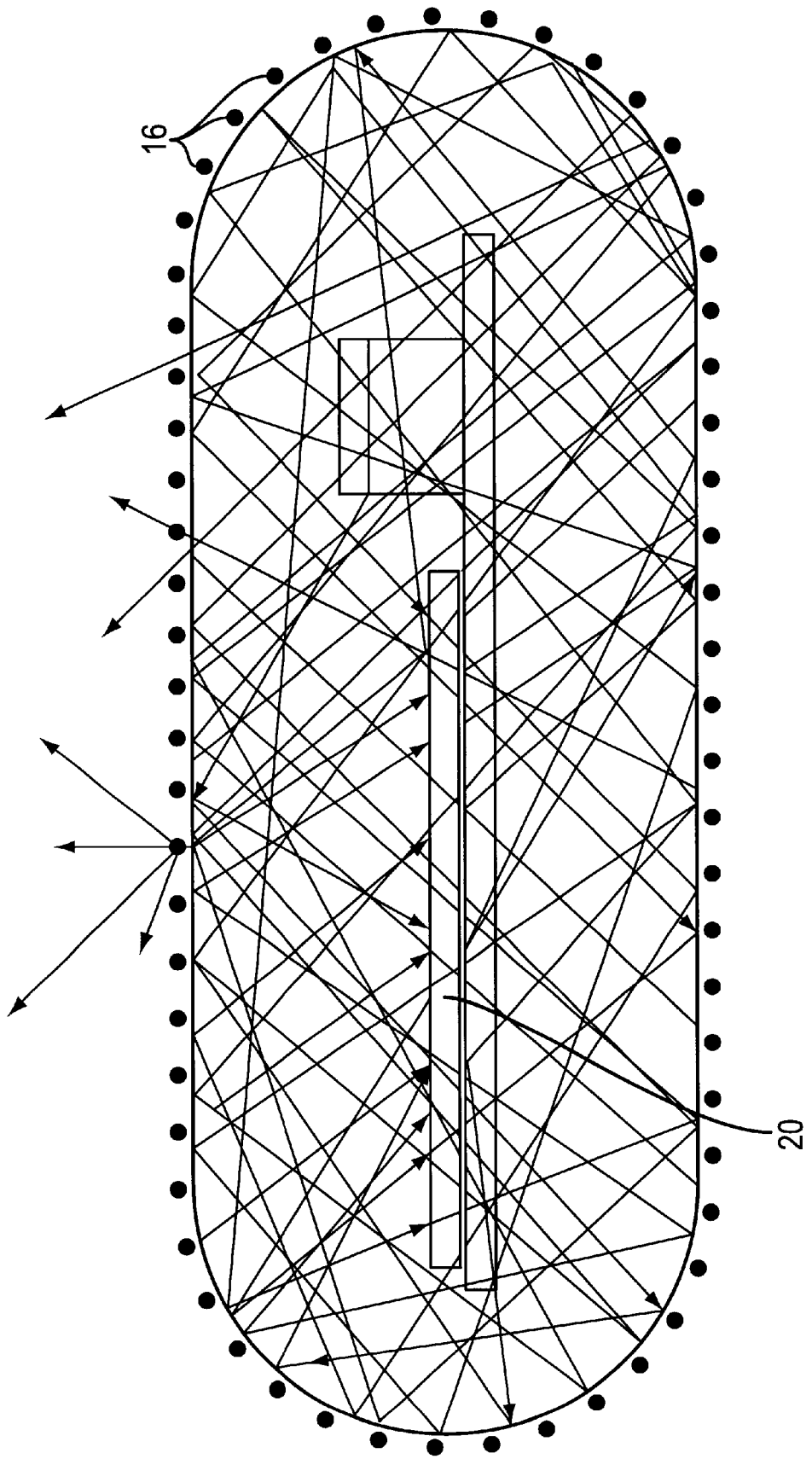
FIG. 4 is schematic diagram, similar to FIG. 2, illustrating reflection within the sensor body by radiation generated by an internal radiation source and by fluorescent light emitted by external indicator molecules.

As demonstrated by FIGS. 3 and 4, at least some of the light emitted by the fluorescent indicator molecules 16 enters the sensor body 12, either directly or after being reflected by the outermost surface (with respect to the sensor body 12) of the matrix layer 14, as illustrated in region 30.

Such fluorescent light 28 is then reflected internally throughout the sensor body 12, much like the radiation emitted by the radiation source 18 is, and, like the radiation emitted by the radiation source, some will strike the interface between the sensor body and the surrounding medium at angles too small to be reflected and will pass back out of the sensor body. Internal reflection of radiation emitted by the source 18 and, for fluorescence-based sensors, fluorescent light emitted by the fluorescent indicator molecules 16, illustrated schematically in FIG. 4, impinges on the photosensitive element 20, which senses the level of such internal illumination.

As further illustrated in FIG. 1, the sensor 10 may also include reflective coatings 32 formed on the ends of the sensor body 12, between the exterior surface of the sensor body and the matrix layer 14, to maximize or enhance the internal reflection of the radiation and/or light emitted by fluorescent indicator molecules. The reflective coatings may be formed, for example, from paint or from a metallized material (provided such metallized material does not impede transmission of telemetry signals to and from the sensor, described below).

As still further illustrated in FIG. 1, an optical filter 34 preferably is provided on the light-sensitive surface of the photosensitive element (photodetector) 20. This filter, as is known from the prior art, prevents or substantially reduces the amount of radiation generated by the source 18 from impinging on the photosensitive surface of the photosensitive element 20. At the same time, the filter allows fluorescent light emitted by fluorescent indicator molecules to pass through it to strike the photosensitive region of the detector. This significantly reduces "noise" in the photodetector signal that is attributable to incident radiation from the source 18.

The application for which the sensor 10 according to one aspect of the invention was developed in particular—although by no means the only application for which it is suitable—is measuring various biological analytes in the human body, e.g., glucose, oxygen, toxins, pharmaceuticals or other drugs, hormones, and other metabolic analytes. The specific composition of the matrix layer 14 and the indicator molecules 16 may vary depending on the particular analyte the sensor is to be used to detect and/or where the sensor is to be used to detect the analyte (i.e., in the blood or in subcutaneous tissues). Two constant requirements, however, are that the matrix layer 14 facilitate exposure of the indicator molecules to the analyte and that the optical characteristics of the indicator molecules (e.g., the level of fluorescence of fluorescent indicator molecules) are a function of the concentration of the specific analyte to which the indicator molecules are exposed.

To facilitate use in-situ in the human body, the sensor 10 is formed in a smooth, oblong or rounded shape. Advantageously, it has the approximate size and shape of a bean or a pharmaceutical gelatin capsule, i.e., it is on the order of approximately 500 microns to approximately 0.5 inch in length L and on the order of approximately 300 microns to approximately 0.3 inch in diameter D, with generally smooth, rounded surfaces throughout. This configuration permits the sensor 10 to be implanted into the human body, i.e., dermally or into underlying tissues (including into organs or blood vessels) without the sensor interfering with essential bodily functions or causing excessive pain or discomfort.

Moreover, it will be appreciated that any implant placed within the human (or any other animal's) body—even an implant that is comprised of "biocompatible" materials—will cause, to some extent, a "foreign body response" within the organism into which the implant is inserted, simply by virtue of the fact that the implant presents a stimulus. In the case of a sensor 10 that is implanted within the human body, the "foreign body response" is most often fibrotic encapsulation, i.e., the formation of scar tissue. Glucose—a primary analyte which sensors according to the invention are expected to be used to detect—may have its rate of diffusion or transport hindered by such fibrotic encapsulation. Even molecular oxygen ($O_2$), which is very small, may have its rate of diffusion or transport hindered by such fibrotic encapsulation as well. This is simply because the cells forming the fibrotic encapsulation (scar tissue) can be quite dense in nature or have metabolic characteristics different from that of normal tissue.

To overcome this potential hindrance to or delay in exposing the indicator molecules to biological analytes, two primary approaches are contemplated. According to one approach, which is perhaps the simplest approach, a sensor/tissue interface layer—overlying the surface of the sensor body 12 and/or the indicator molecules themselves when the indicator molecules are immobilized directly on the surface of the sensor body, or overlying the surface of the matrix layer 14 when the indicator molecules are contained therein—is prepared from a material which causes little or acceptable levels of fibrotic encapsulation to form. Two examples of such materials described in the literature as having this characteristic are Preclude™ Periocardial Membrane, available from W. L. Gore, and polyisobutylene covalently combined with hydrophiles as described in Kennedy, "Tailoring Polymers for Biological Uses," *Chemtech,* February 1994, pp. 24–31.

Alternatively, a sensor/tissue interface layer that is composed of several layers of specialized biocompatible materials can be provided over the sensor. As shown in FIG. 3, for example, the sensor/tissue interface layer 36 may include three sublayers 36a, 36b, and 36c. The sublayer 36a, a layer which promotes tissue ingrowth, preferably is made from a biocompatible material that permits the penetration of capillaries 37 into it, even as fibrotic cells 39 (scar tissue) accumulate on it. Gore-Tex® Vascular Graft material (ePTFE), Dacron® (PET) Vascular Graft materials which have been in use for many years, and MEDPOR Biomaterial produced from high-density polyethylene (available from POREX Surgical Inc.) are examples of materials whose basic composition, pore size, and pore architecture promote tissue and vascular ingrowth into the tissue ingrowth layer.

The sublayer 36b, on the other hand, preferably is a biocompatible layer with a pore size (less than 5 micrometers) that is significantly smaller than the pore size of the tissue ingrowth sublayer 36a so as to prevent tissue ingrowth. A presently preferred material from which the sublayer 36b is to be made is the Preclude Periocardial Membrane (formerly called GORE-TEX Surgical Membrane), available from W. L. Gore, Inc., which consists of expanded polytetra-fluoroethylene (ePTFE).

The third sublayer 36c acts as a molecular sieve, i.e., it provides a molecular weight cut-off function, excluding molecules such as immunoglobulins, proteins, and glycoproteins while allowing the analyte or analytes of interest to pass through it to the indicator molecules (either coated directly on the sensor body 12 or immobilized within a matrix layer 14). Many well known cellulose-type membranes, e.g., of the sort used in kidney dialysis filtration cartridges, may be used for the molecular weight cut-off layer 36c.

Although the sensor/tissue interface layer 36 is described and shown in FIG. 3 as including a third, molecular weight cut-off layer 36c, it will be appreciated that it is possible to select a polymer from which to make the matrix layer 14, e.g., a polymethylmethacrylate or a hydrated hydrophilic acrylic, such that it performs the molecular weight cut-off function without the need for a separate sublayer 36c. It is recommended, however, that the two sublayers 36a and 36b be used, with the outer layer 36a promoting tissue ingrowth and the inner layer 36b preventing tissue ingrowth, because the inner layer 36b functions as an additional barrier (or "prefilter") between the outer layer 36a and the molecular weight cut-off layer (whether provided separately or by the matrix layer 14 itself). This reduces the likelihood of the molecular weight cut-off layer becoming clogged or fouled by macromolecules such as immunoglobulins, extracellular matrix proteins, lipids, and the like, and thereby maximizes the speed and efficiency with which the analyte or analytes of interest come into contact with the indicator molecules. (In order for a sensor to be useful for in vivo testing, the analyte exposure lag time, i.e., the amount of time it takes for the concentration of analyte to which the indicator molecules are directly exposed to come to a steady state, must be relatively short, i.e., on the order of two to five minutes.) Various combinations and permutations of biocompatible materials from which to construct the sensor/tissue interface layer will be apparent to those having skill in the medical implant art.

Finally, with respect to the sensor/tissue interface layer, in addition to preventing adverse reactions, it is believed that the interface layer enhances reflection of light (whether from fluorescent indicator molecules or from the radiation source 18) from the outermost surface of the matrix layer 14 and into the sensor body 12.

A further aspect of a sensor according to the invention is that it may be wholly self-contained. In other words, in specific embodiments, the sensor may be constructed in such a way that no electrical leads extend into or out of the sensor body to supply power to the sensor (e.g., for driving the source 18) or to transmit signals from the sensor. Rather, a sensor according to this aspect of the invention may include a power source 40 (FIG. 1) that is wholly embedded or encapsulated within the sensor body 12 and a transmitter 42 (FIG. 1) that also is entirely embedded or encapsulated within the sensor body 12.

(The shape of the sensor 10 has been found in and of itself to provide superior optical properties, however. Accordingly, embodiments of the sensor having power and/or signal-transmitting leads extending into and/or out of the sensor body are also within the scope of the invention.)

Figure 5:
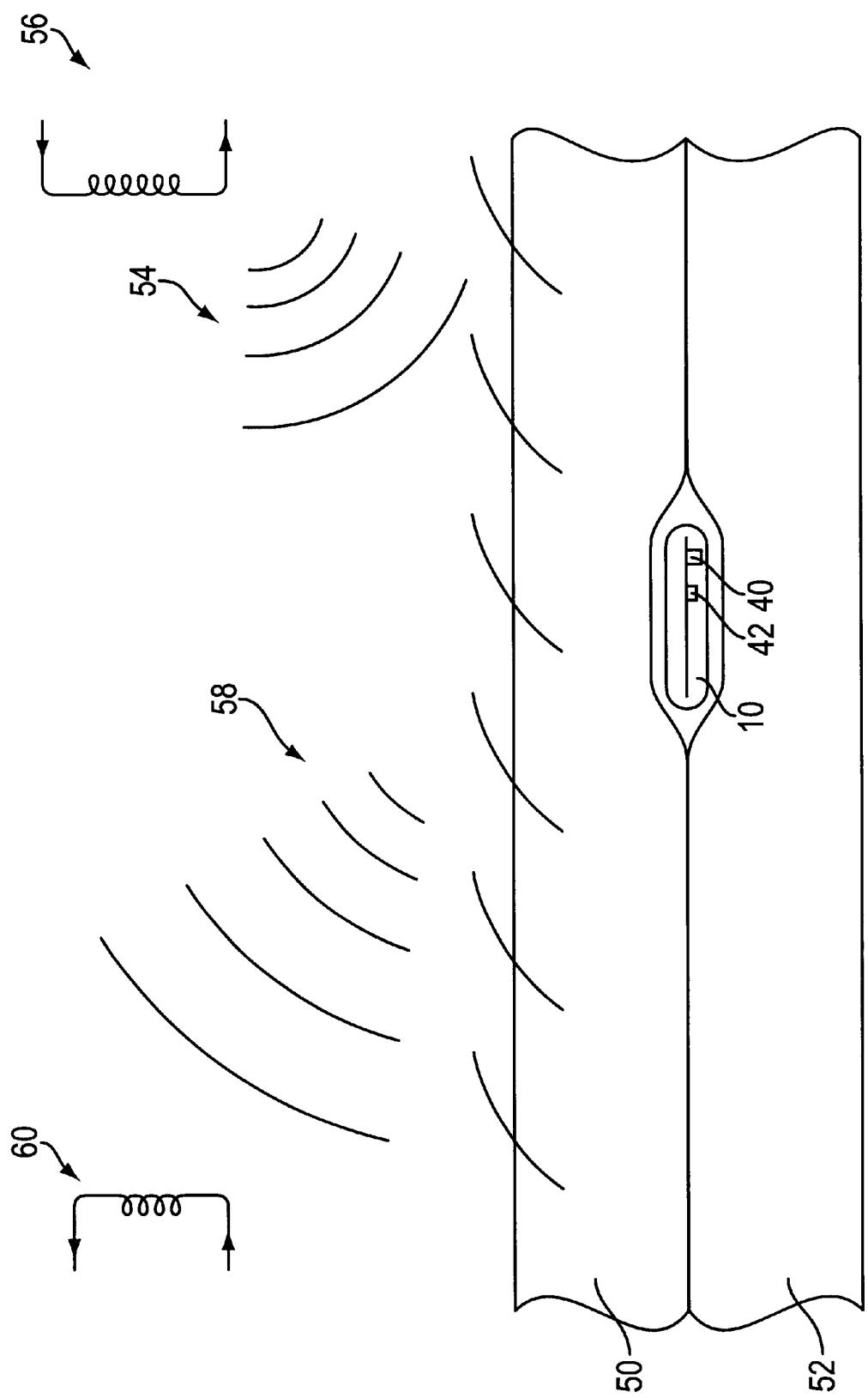
FIG. 5 is a schematic diagram demonstrating use of a sensor according to the invention in a human being.

In a preferred embodiment, the power source 40 is an inductor, as is the transmitter 42. Thus, when the sensor is implanted in the body, e.g. between the skin 50 and subcutaneous tissues 52 as shown in FIG. 5, the sensor can be powered—i.e., the radiation source can be caused to emit radiation which interacts with the indicator molecules 16—by exposing the sensor to a field of electromagnetic radiation 54 created, for example, by an inductor coil 56 that is housed in an appropriately configured instrument (not shown) positioned near the sensor. Similarly, the transmitter 42, as an inductor, generates an electromagnetic field 58 that is indicative of the level of light striking the photosensitive element and hence the presence or concentration of analyte. The field 58 constitutes a signal that can be detected by an external receiver 60. The signal may be, for example, a 50 megahertz carrier, amplitude modulated signal; a frequency modulated signal; a digital signal; or any other type of electromagnetic wave signal that would be known to one having skill in the art.

Alternatively, it is possible to use a single coil and a single inductor for all telemetry. In such an embodiment, the coil 56 generates the electromagnetic wave 54 at one frequency to induce a current in the inductor 40, which powers the source of radiation 18; the amount of internally reflected light sensed by the photosensitive element 20 is transmitted by the same inductor 40 as a modulated electromagnetic wave which induces a current in coil 56. This modulated wave is generated by modulating the current flowing through inductor 40 by the photosensitive element 20 as a function of detected light and is detected by measuring the resulting induced current in coil 56.

Alternatively, the system could be configured to switch (in rapid sequence) between a power generating mode and a signal transmitting mode. These and other telemetry schemes will be familiar to those having skill in the art, as such techniques are used relatively commonly, e.g., in connection with "smart cards" having an implanted integrated circuit chip which can be waved past a sensor to gain access to a building, sometimes referred to as radio frequency identification.

Other contemplated self-contained power sources for driving the radiation source 18 include microbatteries; piezoelectrics (which generate a voltage when exposed to mechanical energy such as ultrasonic sound; micro generators; acoustically (e.g., ultrasound) driven generators; and photovoltaic cells, which can be powered by light (infrared) passing through the skin 50.

Figure 6:
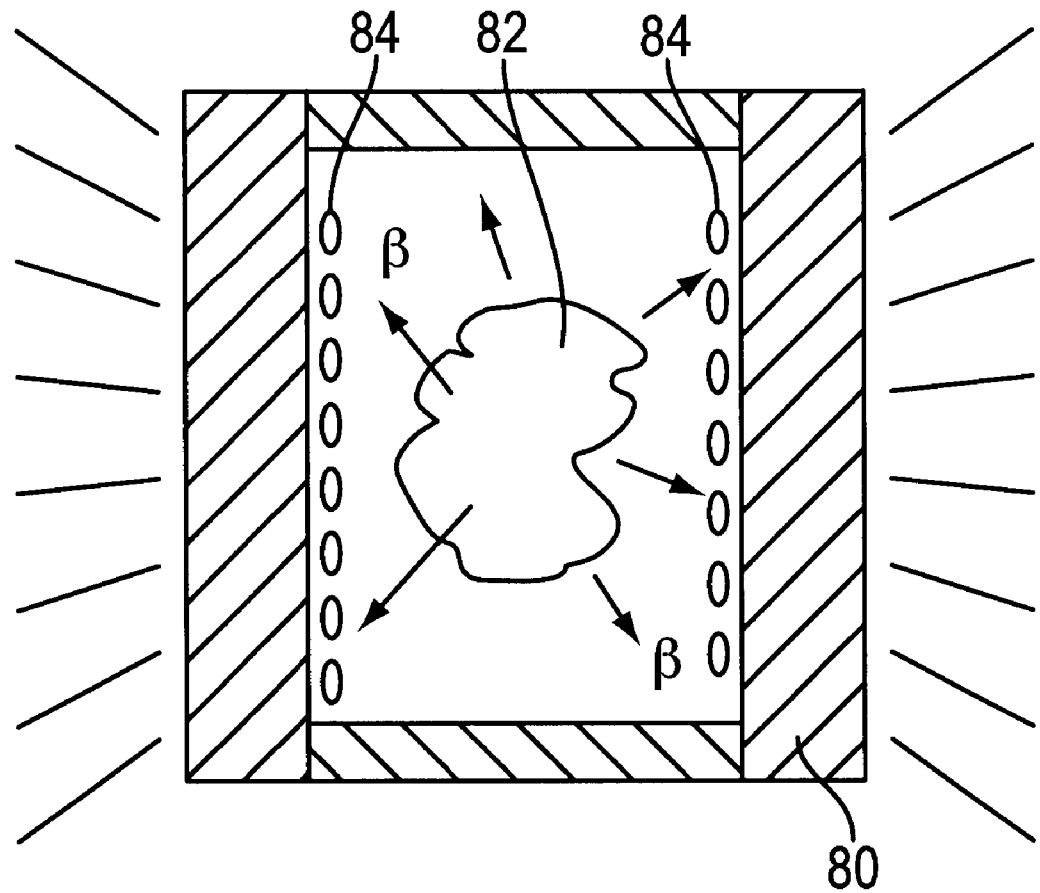
FIG. 6 is a schematic section view of a radioluminescent light source.

As yet another alternative, in place of an LED, a radioluminescent light source can be used. As illustrated in FIG. 6, such a radioluminescent light source includes a sealed, optically transmissive vessel 80 (e.g., cylindrical, spherical, or cubic) with a sample of radioisotope 82, e.g. tritium, contained therein. The radioisotope emits beta particles which strike intermediate luminophore molecules 84 coated on the interior surface of the vessel 80, thereby causing the intermediate luminophore molecules to emit light. Although the beta particles are too weak to pass through the walls of the vessel, the light emitted by the intermediate luminophore molecules does pass through, thereby illuminating the sensor with light—similarly to an LED—that interacts with the indicator molecules. Such radioluminescent generation of light, and similar generation of light, is known in the art. See, for example, U.S. Pat. No. 4,677,008, the disclosure of which is incorporated by reference, and Chuang and Arnold, "Radioluminescent Light Source for Optical Oxygen Sensors," 69 Analytical Chemistry No. 10, 1899–1903, May 15, 1997, the disclosure of which also is incorporated by reference. As another alternative to an LED, the sensor might employ an electroluminscent lamp such as that shown in U.S. Pat. No. 5,281,825.

With respect to the other components shown in FIG. 1, a temperature sensor 64 and an optional signal amplifier 66 are also advantageously provided. The temperature sensor 64 measures the locally surrounding temperature of the ambient tissues and the indicator molecule environment and provides this information to the control logic circuit (not shown). The control logic circuit correlates fluorescence level, for example, with analyte concentration level, thereby correcting the output signal for variations affected by temperature. Amplifier 66 is a relatively simple gain circuit which amplifies the signal generated by the photodetector 20.

To make a sensor according to the invention, the various components and circuitry of the sensor are assembled onto a precut, 0.2 inch by 0.4 inch ceramic (e.g., alumina) substrate 70. The substrate thickness is 0.020 inch. All circuit elements are standard surface mount components available, e.g., from Digi-Key, Garrett, and others. The components are attached to the substrate using standard silver conductive epoxy such as Ablebond-84, available from Ablebond.

Next, a high pass filter may be installed on the photosensitive element by applying a two-part high pass filter epoxy, commonly available from CVI Laser and others. Thickness of the filter is controlled by precision dispensing using a Rainin Micropipettor. The high pass filter epoxy is cured in an oven at 125° C. for two hours, as per the manufacturer's instructions. Similarly, if desired, a low pass filter may be coated over the radiation source (LED) by the same method using a commercially available low pass epoxy formulation. Custom formulations of optical filters can be prepared by adding a dye of the desired absorption spectra into Epotek epoxies. The appropriate concentration of the dopant can be determined by monitoring wavelength versus transmittance on a UV-Vis scan from a spectrophotometer until the desired spectral properties are obtained. Such custom-formulated epoxies can be cured similarly. Prefabricated glass, polymer, or coated filters may also be used and simply glued to the photosensitive element or devices using an optically matching adhesive, as is typical.

The circuit board with optical filters (if installed and cured) is then encapsulated using, e.g., a Lilly No. 4 two-part gelatin capsule as a mold. Other gelatin capsules work as well. The long "half" of an empty capsule is placed upright into a rack. Several drops of optically clear potting of the appropriate sensor body material, as described above, are added to fill the capsule to approximately one half of its volume. The substrate with pre-assembled circuitry is inserted end-on into the capsule and into the optical potting, which wicks around and into the small spaces of the circuit board assembly to help exclude air and thus prevent bubbles from subsequently forming in the finished sensor device. Additional optical potting is added using a micropipettor until the level reaches the top of the capsule with the capsule standing upright. The partial assembly is then further degassed by placing the capsule (supported by the rack) under a bell jar vacuum and allowing it to stand under vacuum until any bubbles observed within the capsule have escaped. The assembly is removed from the vacuum and "topped off" with additional optical potting, allowing surface tension to fill the gelatin capsule-half above its rim and to create a rounded, hemispherical dome shape that is similar to the opposite end.

The capsule is then placed under UV light and cured for several hours, with the curing time depending on the intensity of the UV source available. Heat cure and catalyst cure may alternatively be used, depending on the potting material. A full strength cure is obtained by subsequently incubating the post-UV-cure assembly at 60° C. for 12 hours, or otherwise as per the manufacturer's instructions.

The gelatin mold is then removed from the sensor body by soaking the encapsulated assembly in water for several hours to dissolve the gelatin. Several water changes and washes over the course of the time period help to remove all of the gelatin from the surface. The capsule is then air dried (or oven dried at 60° C.) in preparation for coating.

Once the sensor body is completely dried, it is coated with indicator molecules. The indicator molecules may be immobilized directly on the surface of the sensor body using techniques known in the art, or they may be contained within a matrix layer solution that is coated onto the central body. (A matrix layer solution containing fluorescent indicator molecules may be prepared according to methods known in the art; a matrix layer solution containing light-absorbing indicator molecules may be prepared as described below.) A convenient method for coating the sensor with a matrix layer is to affix a small (e.g., 32 gauge) wire to one end of the encapsulated circuitry to produce a hanger. This can be done using the same UV-cured optical potting material. Approximately one to two microliters of optical potting is placed on the end of the handle wire. The encapsulated circuit is placed in front of a UV lamp with the UV lamp turned off. The wire with optical potting on the tip is touched to the end of the capsule and the lamp is turned on. The small amount of optical potting "adhesive" will be cured immediately, thereby attaching the wire tip to the capsule. The capsule may now be dipped conveniently into matrix layer solutions (and separate indicator molecule solutions, as appropriate) and hung by the wire to cure. The wire may be removed simply by pulling it after the sensor is completely assembled.

Once the indicator molecules are securely bonded to the surface of the sensor body, whether directly thereon or in a matrix layer, the sensor/tissue interface layer is constructed by inserting the sensor body into a preformed tubular sleeve of the material and sealing each end using heat or epoxy or, if the desired sensor/tissue interface layer material is in sheet form, by rolling the sensor body longitudinally in the material and sealing the longitudinal seam and end seams using heat or epoxy.

Although the embodiment of a sensor 10 according to the invention shown and described so far has a single radiation source 18 (LED) and photosensitive element 20 (photodetector), thereby permitting detection of a single analyte, other configurations and components are possible. For example, two or more different types of indicator molecules may be provided to sense the presence or concentration of two or more analytes, respectively, with two or more photosensitive elements being provided on the ceramic substrate 70, each with its own respective transmitter 42. Each photosensitive element would have its own filter 34 designed to allow light from the respective indicator molecules to pass through to it. Similarly, a "two-channel" embodiment could be developed to measure analyte concentration by two different sensing schemes. In one such embodiment for example, some of the indicator molecules would be fluorescent indicator molecules and the rest of the indicator molecules would be radiation-absorbing indicator molecules (as described below). Two separate photosensitive elements would be provided, each with its own appropriate filter—one to measure fluorescent light emitted by the fluorescent indicator molecules and one to measure radiation generated by the source and reflected throughout gelatin with some absorption by the radiation-absorbing indicator molecules. Additionally, other types of photosensitive elements may be used, e.g., photoresistors, phototransistors, photodiodes, photodarlingtons, photovoltaic cells, positive insulating negative photodiodes, large-area photodiodes, avalanche photodiodes, charge coupled devices, etc.

Moreover, although a sensor according to the invention has been described above primarily as functioning based on fluorescence of indicator molecules, the invention is not so limited. According to another aspect of the invention, a sensor construct as per the invention may operate based on the light-absorbing characteristics of light-absorbing indicator molecules. A sensor according to this aspect of the invention could use a sensor construct like that shown in U.S. Pat. No. 5,517,313, referenced above; more preferably, it uses a bean- or pharmaceutical gelatin capsule-shaped construct as described above.

Figure 7B:
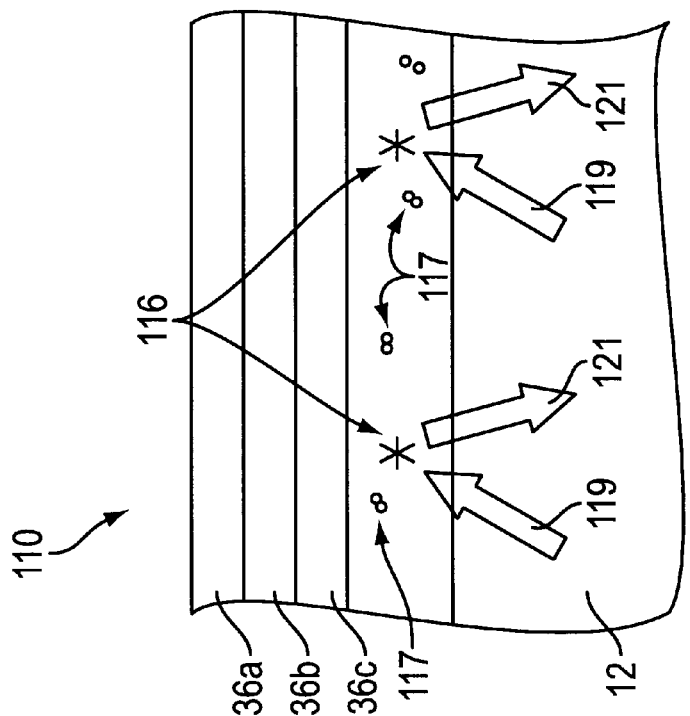
FIGS. 7a and 7b are schematic illustrations demonstrating the operation of a light-absorbing indicator molecule-based sensor according to another aspect of the invention.
Figure 7A:
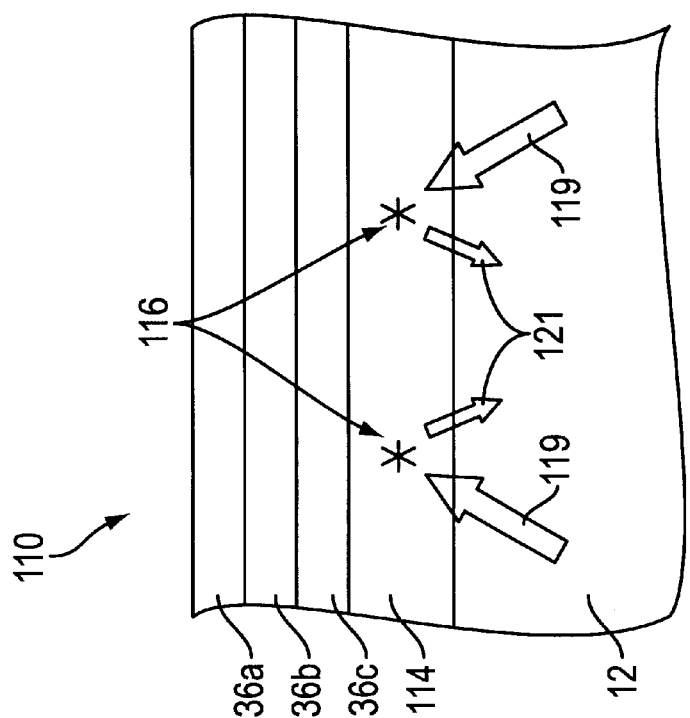

As illustrated in FIGS. 7a and 7b, when a sensor 110 according to this aspect of the invention is not exposed to any analyte, the light-absorbing indicator molecules 116 (which preferably are immobilized in a matrix layer 114) absorb a certain amount of radiation (light) 119 generated by the radiation source, falling within a particular range of wavelengths, and passing out of the sensor body, and non-absorbed radiation 121 is reflected back into the sensor body. When the sensor 110 is exposed to analyte such that the light-absorbing indicator molecules 116 are exposed to analyte molecules 117, the light-absorbing properties of the indicator molecules are affected. For example, as shown in FIG. 7b, the light-absorbing capacity of the indicator molecules 116 may decrease such that the intensity of the light 121 reflected back into the sensor body 12 increases. The level of light within the sensor body is measured by a photosensitive element (not shown), as described above.

It will be appreciated that a light-absorbing indicator molecule-based sensor must be calibrated by determining the illumination intensity levels for various known concentrations of various analytes of interest. Furthermore, because the radiation (light) being measured is the radiation being emitted by the source itself, it will be further appreciated that if the radiation source has a very broad emission profile and the light-absorbing indicator molecule has a very narrow range of absorption wavelengths, a high-pass, low-pass, or band-pass filter may be provided over the photosensitive element so as to permit only this range of radiation wavelengths to be sensed by the photosensitive element.

Indicator molecules whose light-absorbing properties are affected by various analytes are known in the art. (As noted above, however, it is believed that such light-absorbing indicator molecules have not been used in connection with a sensor construct either like that taught herein or in U.S. Pat. No. 5,517,313.) For example, U.S. Pat. No. 5,512,246 discloses light-absorbing indicator molecules whose ability to absorb light varies as a function of the local concentration of glucose. In particular, as the local concentration of glucose increases, the ability of the indicator molecules to absorb light at a wavelength of 515 nanometers decreases. Therefore, if such indicator molecules are used in connection with a bean- or cold capsule-shaped sensor construct as disclosed herein, the level of internal illumination by light at that wavelength will increase. The local glucose concentration level can then be determined from the level of illumination at that wavelength.

Light-absorbing indicator molecules which are responsive to other analytes are well known in the art, e.g., as exemplified by phenolphthalein, which changes color in response to a change in pH.

As is the case with a fluorescent indicator molecule-based sensor, a sensor which utilizes light-absorbing indicator molecules could have the indicator molecules disposed directly on the surface of the sensor body. It is preferred, however, that the indicator molecules be immobilized within a matrix layer 114, as is shown in FIGS. 7a and 7b.

The matrix layer 114 may be manufactured by the low density polymerization of various organic monomers, including hydroxethylmethacrylate (HEMA). HEMA is widely available from sources such as PolySciences in Warrington, Pa. and Sigma in St. Louis, Mo., and may be polymerized by means of heating or exposing the monomers to ultraviolet light, as widely known and understood in the art.

In a preferred embodiment, the light-absorbing indicator molecules 116 are immobilized within the matrix layer 114 by reacting the HEMA with a doped monomer, e.g., aminoethylmethacrylate (AEMA). During polymerization, AEMA introduces a pendant amine group into the matrix layer 114. Monomers other than AEMA also may be used during the manufacture of the matrix layer 114, including aminopropylmethacrylate (APMA) and other commercially available monomers having different pendant groups and varying carbon chain lengths between the amino group and the rest of the monomer. In addition to monomers containing primary amine groups (e.g., AEMA), monomers containing secondary amine groups also may be used for forming the matrix layer 114. Alternatively, pendant cross-linker groups other than amine groups also may be used to covalently link the indicator molecules 116 to the polymer material of the matrix layer 114. Examples of alternative pendant cross-linker groups include sulfhydryl (—SH), carboxyl (COOH), aldehyde (COH), hydroxyl (OH), cyano (CN), ether, and epoxyl groups.

Figure 8:
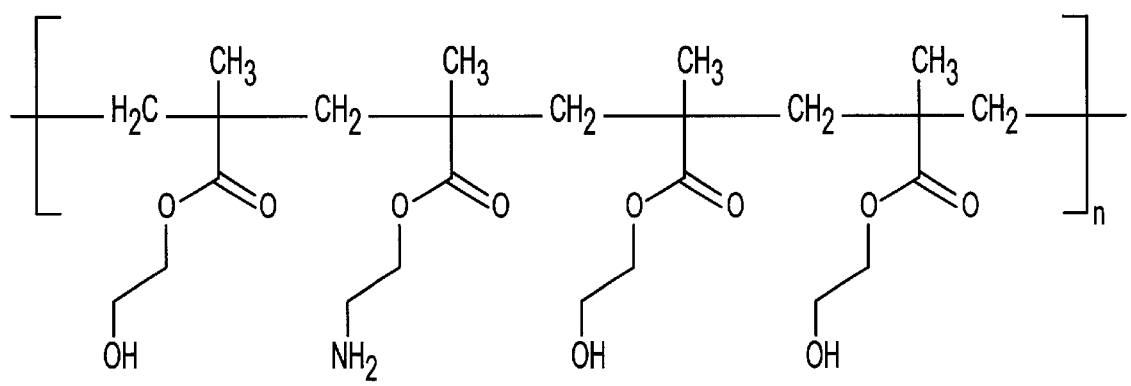
FIG. 8 is a formula for an embodiment of the matrix layer, wherein the polymerized macromolecule of the matrix layer contains a pendant amino group on about every one of four monomers.

Although a range of doping ratios may be used to immobilize the indicator molecules 116, a doping ratio of about 1:4 to about 1:20 AEMA to HEMA is preferred. The matrix layer 114 is provided so as to have stoichiometrically one pendant amino group for every three HEMA residues in the overall polymerized macromolecule of the matrix layer 114. This is illustrated by the formula in FIG. 8.

The polymer material of the matrix layer 114 may be cross-linked by standard cross-linking methods known in the art, including in a preferred embodiment a method using as a cross-linker group a bifunctional poly(ethylene glycol) (n) dimethacrylate. The cross-linker group may be added as per standard practice during the initial formulation of the monomer. This and other cross-linker groups are commercially available from PolySciences (Warrington, Pa.). Although the variable (n) may range from 1 to more than 1000, in a preferred embodiment of the invention, n=1000. The variable (n) may vary depending on the desired density, porosity, and hydrophilic properties of the matrix layer 114.

Figure 9:
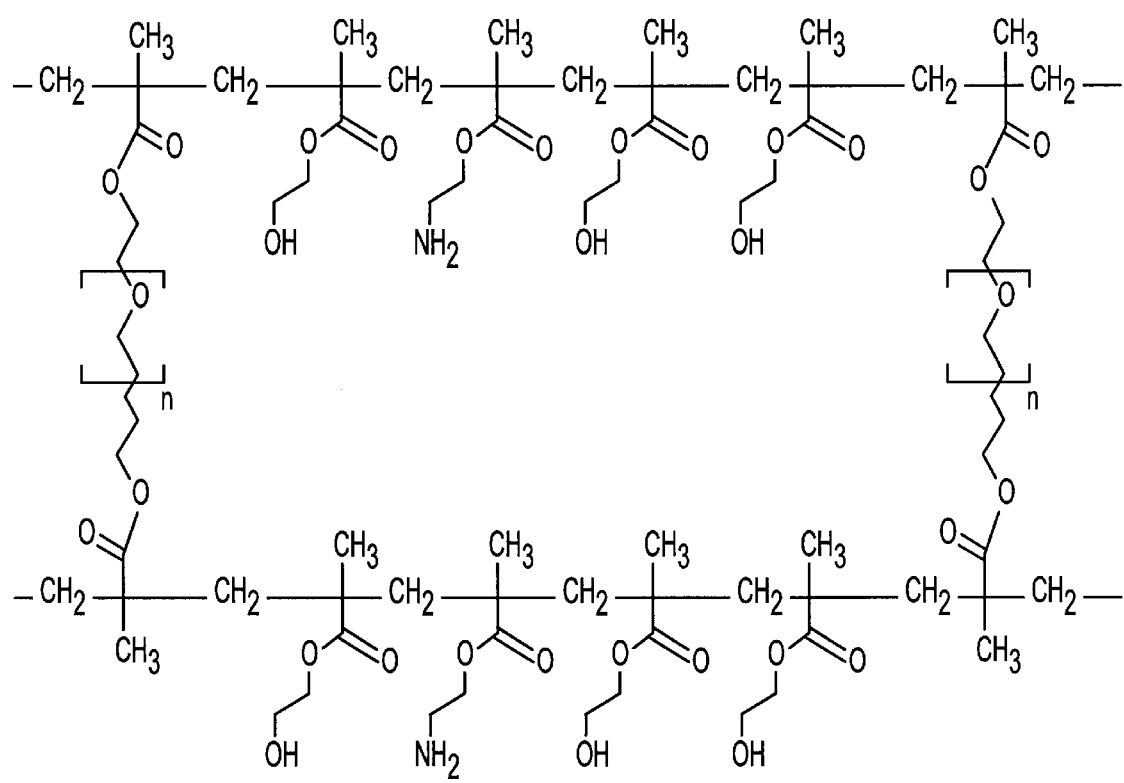
FIG. 9 illustrates a cross-linked and doped segment of the matrix layer in accordance with the present invention.

FIG. 9 illustrates a segment of the matrix layer 114 in accordance with a preferred embodiment of the present invention, which includes a pendant amino doped monomer (AEMA), a HEMA backbone, and a bifunctional cross-linker group.

The matrix layer 114 offers several advantages to the present invention, including allowing access of the analyte (e.g., glucose) to the light-absorbing indicator molecules 116; immobilizing the indicator molecules 116 to prevent them from leaching; maintaining the stability of the optical system of the invention; minimizing the amount of non-specific binding to the porous matrix of molecules other than the desired analyte; restricting access of molecules larger than the desired analyte; and permitting the porous matrix material to support one or more additional, biocompatible interface layers. The matrix layer 114 also is optically compatible with the sensor body 12 and is able to transmit excitation, emission, absorbance, or refractive index wavelength(s) of the indicator molecules 116.

Various methods for immobilizing the indicator molecules 116 within the matrix layer 114 are described in the literature and may range from mechanical entrapment to covalent immobilization. See, for example, A. P. Turner, *Biosensors,* pp. 85–99, Oxford Science Publications, 1987.

Figure 10:
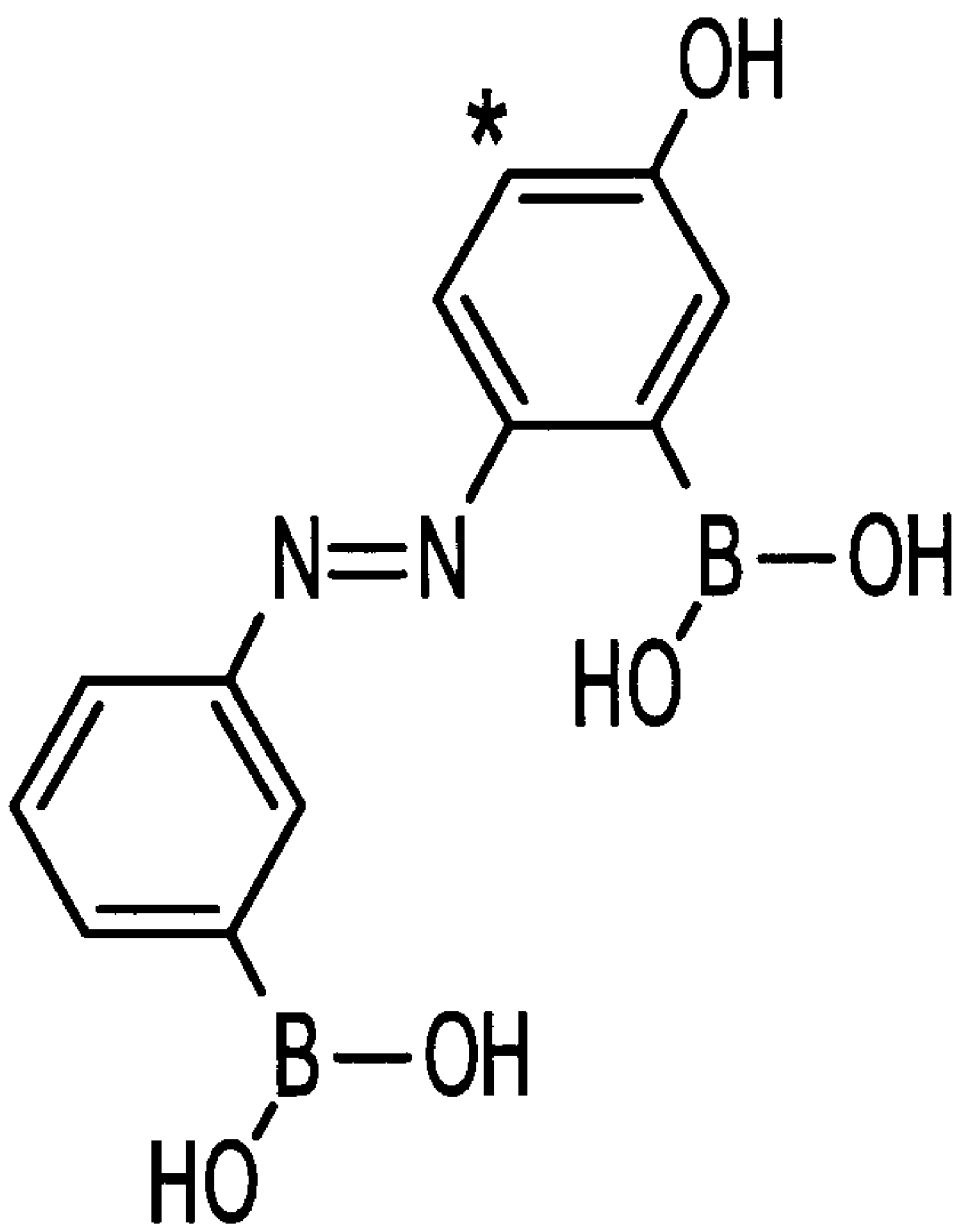
FIG. 10 depicts a glucose-sensitive, absorbance-modulated indicator molecule, 2,3'-dihydroxyboron-4-hydroxy-azobenzene ("Boronate Red") in accordance with the present invention.

In a preferred embodiment, the indicator molecule 116 is a glucose-sensitive, absorbance-modulated indicator molecule which may be covalently immobilized within the matrix layer 114. During polymerization, the indicator molecule 116 covalently attaches to the polymer backbone through a primary amine pendant group, and together they form the matrix layer 114. This form of immobilization is adaptable to various methods using different types of indicator molecules and different pendant groups on the polymer backbone. Examples of glucose-sensitive, absorbance-modulated indicator molecules include 2,3'-dihydroxyboron-4-hydroxy-azobenzene (also known as "Boronate Red"), as depicted in FIG. 10. Glucose can interact with the indicator molecules 116, as described in U.S. Pat. No. 5,512,246. Another similarly prepared preferred indicator molecule 116 for use in the present invention is depicted in FIG. 11.

Figure 11:
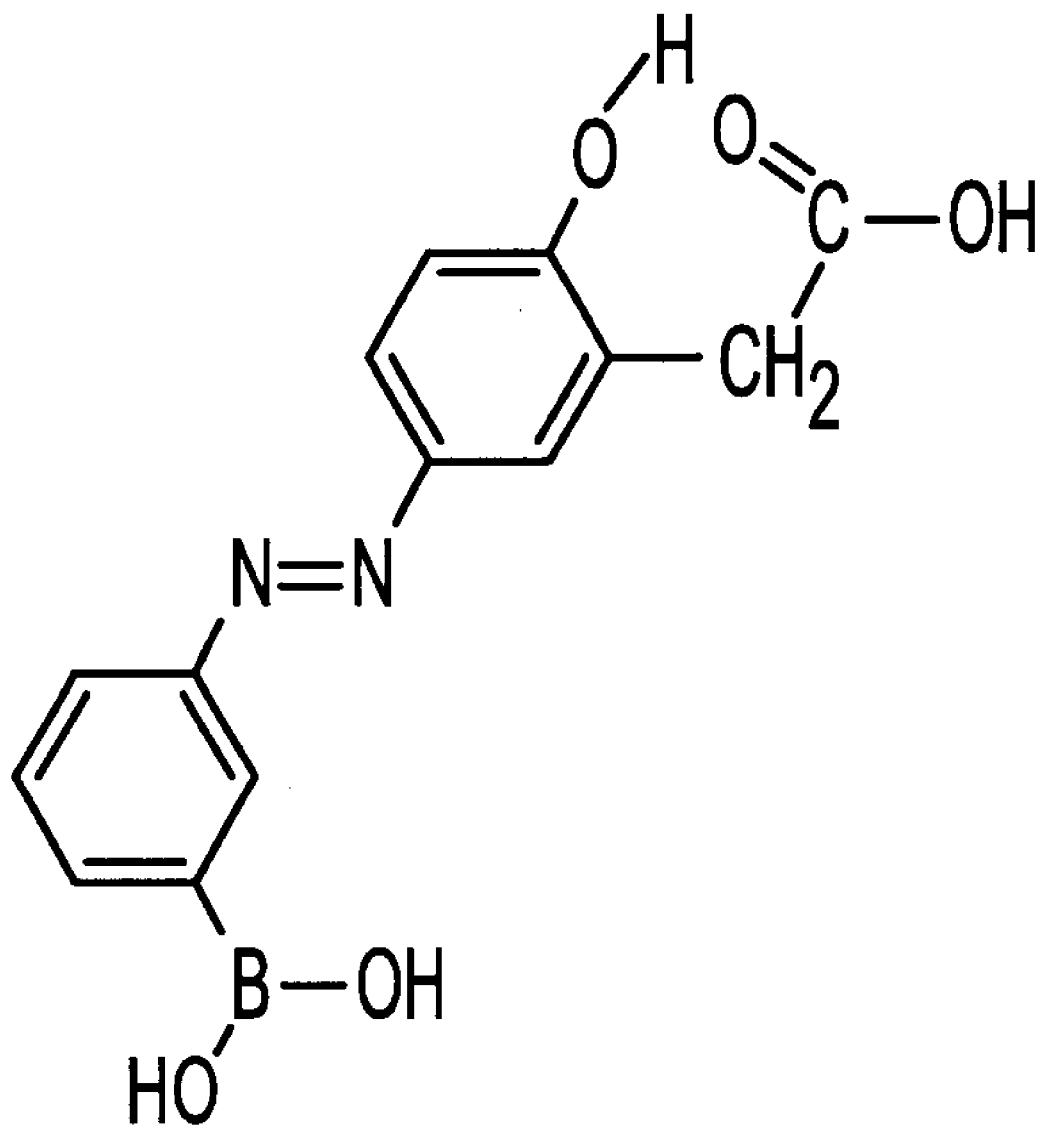
FIG. 11 depicts an additional embodiment of a glucose-sensitive, absorbance-modulated indicator molecule in accordance with the present invention.
Figure 12:
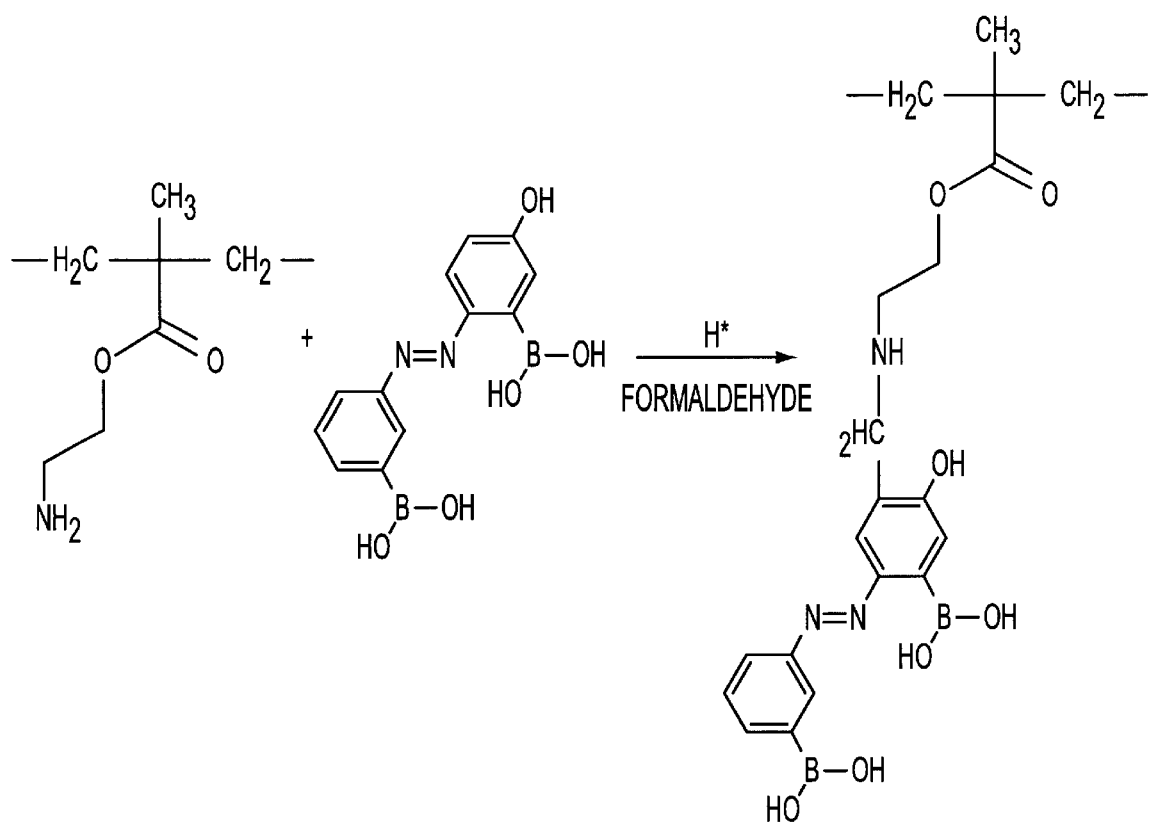
FIG. 12 depicts a standard Mannich reaction for linking the indicator molecule and the doped monomer AEMA.

In a preferred method of immobilizing the indicator molecules 116 shown in FIGS. 10 and 11 in the matrix layer 114, the ortho hydrogen position of the phenol group (represented by an "*" in the indicator molecules depicted in FIGS. 10 and 11) is aminoalkylated using the Mannich reaction, which is known in the organic chemistry art as a reaction wherein certain hydrogens of ketones, esters, phenols, and other organic compounds may be condensed in the presence of formaldehyde and an amine. The reagents for performing the Mannich reaction are commercially available from many chemical supply companies, including Pierce Chemicals. A standard Mannich reaction for linking the indicator molecule 116 to AEMA is depicted in FIG. 12. By copolymerizing AEMA and HEMA into the polymer backbone of the matrix layer 114, the indicator molecule 116 can be linked to the polymer material of the matrix layer 114 and rendered accessible to the analyte, e.g., glucose.

The indicator molecule 116 may be linked to the polymer material of the matrix layer 114 in various ways, including first coupling the indicator molecule 116 to AEMA prior to co-polymerization with HEMA. Alternatively, non-covalent, mechanical entrapment of the indicator molecule 116 may be used by first immobilizing the indicator molecule 116 to pendant amine groups of polylysine. The preimmobilized polylysine/indicator molecule precursor can then be mixed with HEMA prior to polymerization. Upon polymerization of the methacrylate, the polylysine/indicator molecule complex is trapped within the methacrylate matrix, while at the same time the indicator molecule 116 remains covalently immobilized to polylysine.

The sensor 110 otherwise is constructed as described above.

A sensor according to a third aspect of the invention takes advantage of the bean- or pharmaceutical gelatin capsule-shaped construct described above (although by no means is limited to such a construct) to facilitate sensing the presence or concentration of an analyte based on changes in the refractive index of the medium in which the sensor is disposed (or the refractive index of a matrix encapsulating the sensor, if one is used). In general, light traveling through a first medium having a refractive index $n_1$ will pass across the interface between the first medium and a second medium having a refractive index $n_2$ if the angle of incidence of the light striking the interface (measured relative to a normal to the interface) is less than the critical angle $\theta_c$; light striking the interface at an angle of incidence greater than the critical angle, on the other hand, will be reflected internally within the first medium. The critical angle $\theta_c = \sin^{-1}(n_2/n_1)$. Thus, for the limiting case of $n_1 >> n_2$ such that $(n_2/n_1)$ approaches 0 and the critical angle approaches 0°, light will be virtually entirely internally reflected within the first medium. Conversely, for the limiting condition of $n_1 = n_2$ such that the critical angle=90°, there will be no internal reflection within the first medium and all light will pass across the interface into the second medium.

Figure 13B:
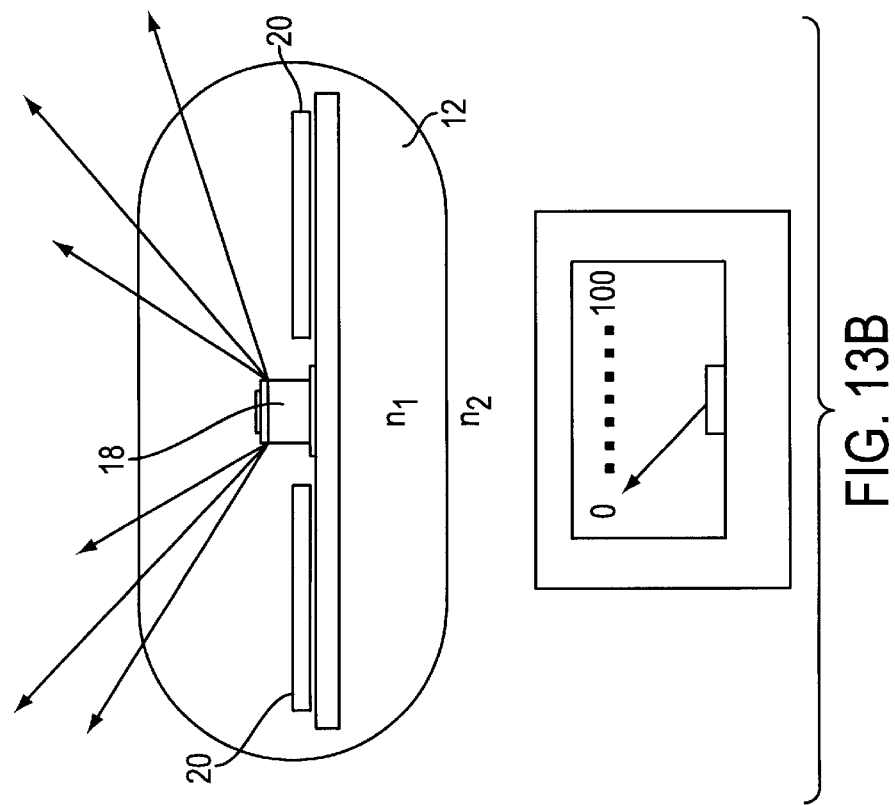
FIGS. 13a and 13b are schematic illustrations demonstrating the operating principle of a refractive index-based sensor according to another aspect of the invention.
Figure 13A:
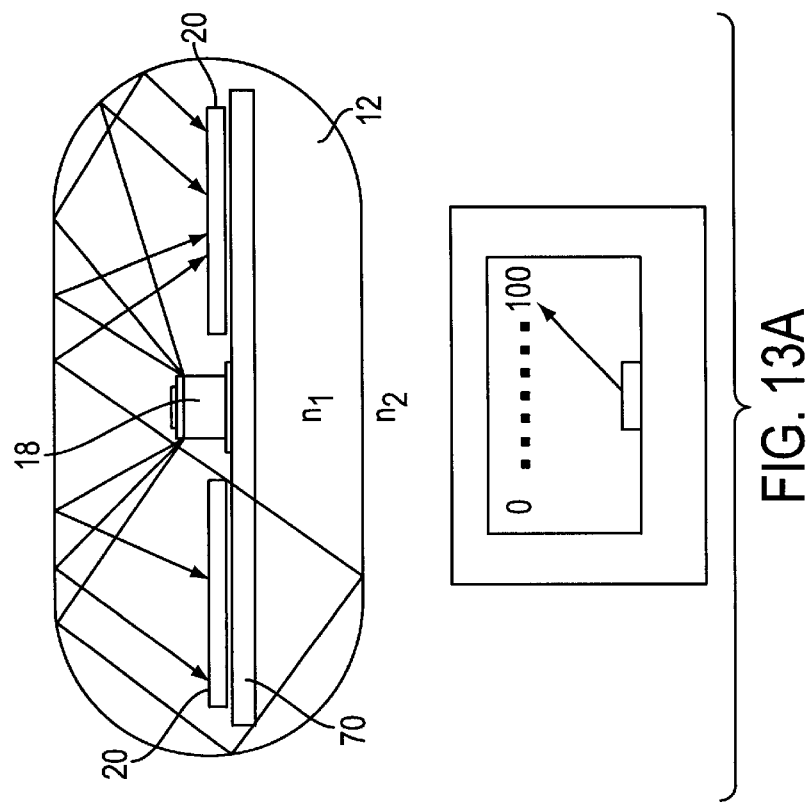

This principle is illustrated schematically in FIGS. 13a and 13b in the context of a sensor construct as taught herein. In FIG. 13a, the refractive index $n_1$ of the sensor body 12 is substantially larger than the refractive index $n_2$ of the surrounding medium. Therefore, all of the internal light generated by the source 18—which light, because of the waveguide properties of the sensor body, will have all possible angles of incidence from 0° to 90°—striking the interface at angles other than perfectly perpendicular will be internally reflected within the sensor body and will be sensed by the photosensitive elements 20. As shown in FIG. 13b, in contrast, where the refractive index $n_2$ is equal to the refractive index of the sensor body 12, the critical angle will be 90° (i.e., tangent to the interface between the sensor body and the surrounding medium), and therefore all light generated by the source 18 will pass out of the sensor body 12 and none (or almost none) will be sensed by the photosensitive elements 20.

It is possible to capitalize on the relationship between the critical angle and the relative refractive indices to determine the concentration of an analyte to which the sensor is exposed because, in general, the refractive index of a medium increases with the density of the medium. For example, if the sensor body is encapsulated in a membrane (not shown) which is selectively permeable (via size exclusion, charge exclusion, or permselectivity) to the analyte of interest, the density of the membrane will increase as analyte diffuses into it. This allows more light to pass out of the sensor body and causes less light to strike the photosensitive elements. In other words, with increasing analyte concentration, the level of internal reflection will decrease, and this decrease can be measured and correlated to the local analyte concentration.

It should be noted that some biological materials such as proteins, hormones, etc. do not dissolve in water and therefore will not permeate the membrane. Glucose, salts, and other small molecular weight compounds, however, are the primary metabolic analytes which will diffuse into the membrane and therefore are the analytes a refraction-based sensor could be used most effectively to measure.

In the most basic embodiment of a refraction-based sensor, a surrounding membrane would not need to be used. Such a basic embodiment could be used where the only matter varying in concentration is the analyte of interest. For example, as champagne or wine ages, the sugar content decreases, as does the density and hence the refractive index of the fluid. Therefore, a sensor according to this aspect of the invention could be placed in a bottle of champagne or a cask of wine as it is processing and used to measure sugar content as the champagne or wine develops. Other potential applications are determining the liquid level inside a vessel or determining the amount of moisture in fuel oil.

Finally, although specific embodiments of the various aspects of the invention have been described above, it will be appreciated that numerous modifications and variations of these embodiments will occur to those having skill in the art. Such modifications and variations and are deemed to be within the scope of the following claims.

We claim:

1. An optical-based sensor for determining the presence or concentration of an analyte in a medium, said sensor comprising:

an optically transmissive sensor body which functions as an optic wave guide, said sensor body having a surface;

a radiation source which emits radiation, said radiation source being embedded within said sensor body such that radiation emitted by said source travels within said sensor body;

fluorescent indicator molecules disposed on the surface of said sensor body, said indicator molecules emitting fluorescent light in response to radiation emitted by the radiation source, the level of fluorescence varying with the concentration of the analyte to which said indicator molecules are exposed; and a photosensitive element which is responsive to fluorescent light emitted by said indicator molecules, said photosensitive element being embedded within said sensor body;

wherein radiation emitted by said source passes out of said sensor body, at least some of the radiation passing out of said sensor body being reflected internally within said sensor body before passing out of said sensor body;

wherein said indicator molecules fluoresce in response to radiation emitted by said source which passes out of said sensor body; and wherein at least some of the fluorescent light emitted by said indicator molecules passes into said sensor body and is detected by said photosensitive element, at least some of the fluorescent light detected by said photosensitive element being reflected internally within said sensor body before striking said photosensitive element.

2. The sensor of claim 1, wherein said indicator molecules are disposed within a matrix layer coated on the surface of said sensor body, said matrix layer being permeable to the analyte and said matrix layer permitting radiation emitted by the radiation source to enter therein.

3. The sensor of claim 1, further comprising a filter which allows fluorescent light emitted by said indicator molecules and passing into said sensor body to strike said photosensitive element, said filter substantially preventing radiation emitted by said source from striking said photosensitive element.

4. The sensor of claim 1, further comprising a power source which powers said radiation source to cause said radiation source to emit radiation, said power source being embedded within said sensor body.

5. The sensor of claim 4, wherein said power source comprises an inductor and said radiation source is caused to emit radiation by exposing the sensor to a field of electromagnetic radiation that is generated exterior to said sensor body.

6. The sensor of claim 1, further comprising a transmitter embedded within said sensor body, said transmitter transmitting from within said sensor body to the exterior of said sensor body a signal indicative of the concentration of the analyte.

7. The sensor of claim 6, wherein said transmitter comprises an inductor which generates a field of electromagnetic radiation that is detectable by a signal pickup device that is located exterior to said sensor body.

8. The sensor of claim 4, further comprising a transmitter embedded within said sensor body, said transmitter transmitting from within said sensor body to the exterior of said sensor body a signal indicative of the concentration of the analyte.

9. The sensor of claim 8, wherein said embedded power source powers both said radiation source and said transmitter.

10. The sensor of claim 1, wherein said sensor has an oblong, rounded shape whereby said sensor can be disposed within the body of a living human.

11. The sensor of claim 10, wherein said sensor has an overall length of approximately 500 microns to approximately 0.5 inch and a diameter of approximately 300 microns to approximately 0.3 inch.

12. The sensor of claim 1, wherein the level of fluorescence of said indicator molecules varies as a function of the concentration of oxygen.

13. The sensor of claim 1, further comprising a tissue/sensor interface layer disposed over said indicator molecules, said tissue/sensor interface layer being permeable to the analyte.

14. The sensor of claim 13, wherein said tissue/sensor interface layer retards formation of fibrotic encapsulation or scar tissue.

15. The sensor of claim 13, wherein said tissue/sensor interface layer comprises a sublayer which promotes tissue ingrowth therein.

16. The sensor of claim 15, wherein said tissue ingrowth comprises vascularization.

17. The sensor of claim 13, wherein said tissue/sensor interface layer comprises a molecular sieve sublayer which performs a molecular weight cutoff function.

18. The sensor of claim 13, wherein said tissue/sensor interface layer is selectively permeable so as to permit said analyte to contact said indicator molecules while preventing cells or macromolecules from contacting said indicator molecules.

19. The sensor of claim 13, wherein said tissue/sensor interface layer is biocompatible.

20. The sensor of claim 1, further comprising a reflection enhancement layer disposed over a portion of the surface of said sensor body to enhance reflection within said sensor body of radiation emitted by said source and/or fluorescent light emitted by said indicator molecules and passing into said sensor body.

21. The sensor of claim 1, wherein said radiation source comprises a light-emitting diode.

22. The sensor of claim 1, wherein said radiation source comprises a radioluminescent light source.

23. The sensor of claim 1, wherein said indicator molecules interact with the radiation emitted by said radiation source by means of evanescent excitation.

24. The sensor of claim 1, wherein said indicator molecules interact with the radiation emitted by said radiation source by means of surface plasmon resonance-type excitation.

25. An optical-based sensor for determining the presence or concentration of an analyte in a medium, said sensor comprising:

a sensor body having a surface;

a matrix layer disposed on the surface of said sensor body, said matrix layer being permeable to the analyte and comprising fluorescent indicator molecules which fluoresce in response to radiation, the level of fluorescence being a function of the concentration of the analyte to which said indicator molecules are exposed, said matrix layer permitting radiation with which said indicator molecules interact to enter therein;

a radiation source which emits radiation that causes said indicator molecules to fluoresce, said radiation source being disposed such that radiation emitted thereby passes from said sensor body into said matrix layer and causes said indicator molecules to fluoresce; and a photosensitive element which senses fluorescent light emitted by said indicator molecules and disposed so as to detect such emitted fluorescent light, said photosensitive element configured to provide a response signal indicative of the amount of such detected fluorescent light and hence the presence or concentration of said analyte.

26. The sensor of claim 25, wherein said sensor has an oblong, rounded shape with an overall length of approximately 500 microns to approximately 0.5 inch and a diameter of approximately 300 microns to approximately 0.3 inch, whereby said sensor can be disposed within the body of a living human without causing excessive or intolerable levels of discomfort.

27. An optical-based sensor for determining the presence or concentration of an analyte in a medium, said sensor comprising:
   an optically transmissive sensor body which functions as an optic wave guide, said sensor body having a surface;
   fluorescent indicator molecules disposed on the surface of said sensor body, said indicator molecules fluorescing in response to radiation, the level of fluorescence being a function of the concentration of the analyte to which said indicator molecules are exposed;
   a radiation source which emits radiation that causes said indicator molecules to fluoresce, said radiation source being disposed such that radiation emitted thereby strikes said indicator molecules; and
   a photosensitive element disposed so as to detect fluorescent light emitted by said indicator molecules, said photosensitive element configured to provide a response signal indicative of the amount of fluorescent light detected thereby and hence the presence or concentration of said analyte;
   said sensor further comprising a power source embedded within said sensor body, said power source powering said radiation source to cause said radiation source to emit radiation.
   a photosensitive element disposed so as to detect fluorescent light emitted by said indicator molecules, said photosensitive element configured to provide a response signal indicative of the amount of fluorescent light detected thereby and hence the presence or concentration of said analyte;
   said sensor further comprising a power source embedded within said sensor body, said power source powering said radiation source to cause said radiation source to emit radiation.

28. The sensor of claim 27, further comprising a transmitter embedded within said sensor body which transmits a signal indicative of the level of fluorescent light detected by said photosensitive element.

29. The sensor of claim 28, wherein said embedded power source powers both said radiation source and said transmitter.

30. The sensor of claim 27, wherein said power source comprises an inductor whereby said radiation source is caused to emit radiation by exposing said sensor to a field of electromagnetic radiation generated exterior to said sensor body.

31. An optical-based sensor for determining the presence or concentration of an analyte in a medium, said sensor comprising:
   an optically transmissive sensor body which functions as an optic wave guide, said sensor body having a surface;
   fluorescent indicator molecules disposed on the surface of said sensor body, said indicator molecules fluorescing in response to radiation, the level of fluorescence being a function of the concentration of the analyte to which said indicator molecules are exposed;
   a radiation source which emits radiation that causes said indicator molecules to fluoresce, said radiation source being disposed such that radiation emitted thereby strikes said indicator molecules; and
   a photosensitive element disposed so as to detect fluorescent light emitted by said indicator molecules;
   said sensor further comprising a transmitter embedded within said sensor body which transmits a signal indicative of the level of fluorescent light detected by said photosensitive element and hence the presence or concentration of said analyte.

32. The sensor of claim 31, wherein said transmitter comprises an inductor which generates a field of electromagnetic radiation that is detectable by a signal pickup device that is located exterior to said sensor body.

33. An optical-based sensor for determining the presence or concentration of an analyte in a medium, said sensor comprising:
   an optically transmissive sensor body which functions as an optic wave guide, said sensor body having a surface;
   a radiation source which emits radiation, said radiation source being embedded within said sensor body such that radiation emitted by said source travels within said sensor body;
   radiation-absorbing indicator molecules disposed on the surface of said sensor body, said indicator molecules absorbing radiation emitted by said radiation source, the level of absorption varying with the concentration of the analyte to which said indicator molecules are exposed; and
   a photosensitive element which is responsive to radiation emitted by said radiation source, said photosensitive element being embedded within said sensor body;
   wherein radiation emitted by said source passes out of said sensor body, at least some of the radiation passing out of said sensor body being reflected internally within said sensor body before passing out of said sensor body;
   wherein said indicator molecules absorb at least some of the radiation emitted by said source and passing out of said sensor body and at least some non-absorbed radiation passes back into said sensor body; and
   wherein at least some of said non-absorbed radiation passing back into said sensor body is detected by said photosensitive element, at least some of the non-absorbed radiation detected by said photosensitive element being reflected internally within said sensor body before striking said photosensitive element.

34. The sensor of claim 33, wherein said indicator molecules are disposed within a matrix layer coated on the surface of the sensor body, said matrix layer being permeable to the analyte and said matrix layer permitting radiation emitted by the radiation source to enter therein.

35. The sensor of claim 33, further comprising a filter which allows radiation emitted by said source and at a wavelength absorbed by said indicator molecules to strike said photosensitive element and which substantially prevents radiation emitted by said source and not at a wavelength absorbed by said indicator molecules from striking said photosensitive element.

36. The sensor of claim 33, further comprising a power source which powers said radiation source to cause said radiation source to emit radiation, said power source being embedded within said sensor body.

37. The sensor of claim 36, wherein said power source comprises an inductor and said radiation source is caused to emit radiation by exposing the sensor to a field of electromagnetic radiation that is generated exterior to said sensor body.

38. The sensor of claim 36, further comprising a transmitter embedded within said sensor body, said transmitter transmitting from within said sensor body to the exterior of said sensor body a signal indicative of the concentration of the analyte.

39. The sensor of claim 38, wherein said embedded power source powers both said radiation source and said transmitter.

40. The sensor of claim 33, further comprising a transmitter embedded within said sensor body, said transmitter transmitting from within said sensor body to the exterior of said sensor body a signal indicative of the concentration of the analyte.

41. The sensor of claim 40, wherein said transmitter comprises an inductor which generates a field of electromagnetic radiation that is detectable by a signal pickup device that is located exterior to said sensor body.

42. The sensor of claim 33, wherein said sensor has an oblong, rounded shape whereby said sensor can be disposed within the body of a living human.

43. The sensor of claim 42, wherein said sensor has an overall length of approximately 500 microns to approximately 0.5 inch and a diameter of approximately 300 microns to approximately 0.3 inch.

44. The sensor of claim 33, wherein the level of absorption of said indicator molecules varies as a function of the concentration of glucose.

45. The sensor of claim 33, further comprising a tissue/sensor interface layer disposed over said indicator molecules, said tissue/sensor interface layer being permeable to the analyte.

46. The sensor of claim 45, wherein said tissue/sensor interface layer retards formation of fibrotic encapsulation or scar tissue.

47. The sensor of claim 45, wherein said tissue/sensor interface layer comprises a sublayer which promotes tissue ingrowth therein.

48. The sensor of claim 47, wherein said tissue ingrowth comprises vascularization.

49. The sensor of claim 45, wherein said tissue/sensor interface layer comprises a molecular sieve sublayer which performs a molecular weight cutoff function.

50. The sensor of claim 45, wherein said tissue/sensor interface layer is selectively permeable so as to permit said analyte to contact said indicator molecules while preventing cells or macromolecules from contacting said indicator molecules.

51. The sensor of claim 45, wherein said tissue/sensor interface layer is biocompatible.

52. The sensor of claim 33, further comprising a reflection enhancement layer disposed over a portion of the surface of said sensor body to enhance reflection within said sensor body of radiation emitted by said source.

53. The sensor of claim 33, wherein said radiation source comprises a light-emitting diode.

54. The sensor of claim 33, wherein said radiation source comprises a radioluminescent light source.

55. The sensor of claim 33, wherein said indicator molecules interact with the radiation emitted by said radiation source by means of evanescent excitation.

56. The sensor of claim 33, wherein said indicator molecules interact with the radiation emitted by said radiation source by means of surface plasmon resonance-type excitation.

57. An optical-based sensor for determining the presence or concentration of an analyte in a medium, said sensor comprising:
  a sensor body having a surface;
  a matrix layer disposed on the surface of said sensor body, said matrix layer being permeable to the analyte and comprising indicator molecules which absorb radiation, the level of absorption being a function of the concentration of the analyte to which said indicator molecules are exposed, said matrix layer permitting radiation which said indicator molecules absorb to enter therein;
  a radiation source which emits radiation that is absorbed by said indicator molecules, said radiation source being disposed such that radiation emitted thereby enters said matrix layer and is absorbed by said indicator molecules; and
  a photosensitive element which detects radiation emitted by said radiation source and disposed so as to detect radiation emitted by said radiation source and not absorbed by said indicator molecules, said photosensitive element configured to provide a response signal indicative of the amount of such detected non-absorbed radiation and hence the presence or concentration of said analyte.

58. The sensor of claim 57, wherein said sensor has an oblong, rounded shape with an overall length of approximately 500 microns to approximately 0.5 inch and a diameter of approximately 300 microns to approximately 0.3 inch, whereby said sensor can be disposed within the body of a living human without causing excessive or intolerable levels of discomfort.

59. An optical-based sensor for determining the presence or concentration of an analyte in a medium, said sensor comprising:
  a sensor body having a surface;
  radiation-absorbing indicator molecules disposed on the surface of said sensor body, the level of absorption being a function of the concentration of the analyte to which said indicator molecules are exposed;
  a radiation source which emits radiation that is absorbed by said indicator molecules, said radiation source being disposed such that radiation emitted thereby is absorbed by said indicator molecules; and
  a photosensitive element which detects radiation emitted by said radiation source, said photosensitive element disposed so as to detect radiation emitted by said radiation source and not absorbed by said indicator molecules, said photosensitive element configured to provide a response signal indicative of the amount of non-absorbed radiation detected thereby and hence the presence or concentration of said analyte;
  said sensor further comprising a power source embedded within said sensor body, said power source powering said radiation source to cause said radiation source to emit radiation.

60. The sensor of claim 59, further comprising a transmitter embedded within said sensor body which transmits a signal indicative of the level of non-absorbed radiation detected by said photosensitive element.

61. The sensor of claim 60, wherein said embedded power source powers both said radiation source and said transmitter.

62. The sensor of claim 59, wherein said power source comprises an inductor whereby said radiation source is caused to emit radiation by exposing said sensor to a field of electromagnetic radiation generated exterior to said sensor body.

63. An optical-based sensor for determining the presence or concentration of an analyte in a medium, said sensor comprising:
   a sensor body having a surface;
   radiation-absorbing indicator molecules disposed on the surface of said sensor body, the level of absorption being a function of the concentration of the analyte to which said indicator molecules are exposed;
   a radiation source which emits radiation that is absorbed by said indicator molecules, said radiation source being disposed such that radiation emitted thereby is absorbed by said indicator molecules; and
   a photosensitive element which detects radiation emitted by said radiation source, said photosensitive element disposed so as to detect radiation emitted by said radiation source and not absorbed by said indicator molecules;
   said sensor further comprising a transmitter embedded within said sensor body which transmits a signal indicative of the level of radiation detected by said photosensitive element and hence the presence or concentration of said analyte.

64. The sensor of claim 63, wherein said transmitter comprises an inductor which generates a field of electromagnetic radiation that is detectable by a signal pickup device that is located exterior to said sensor body.

65. An optical-based sensor for determining the presence or concentration of a plurality of analytes in a medium, said sensor comprising:
   an optically transmissive sensor body which functions as an optic wave guide, said sensor body having a surface;
   first and second indicator molecules disposed on the surface of said sensor body, said first indicator molecules having an optical characteristic that is responsive to changes in the concentration of a first analyte to which said first indicator molecules are exposed and said second indicator molecules having an optical characteristic that is responsive to changes in the concentration of a second analyte to which said second indicator molecules are exposed;
   a radiation source which emits radiation that interacts with said first indicator molecules in accordance with the analyte-responsive optical characteristic thereof and a radiation source which emits radiation that interacts with said second indicator molecules in accordance with the analyte-responsive optical characteristic thereof, said radiation source or sources being embedded within said sensor body such that radiation emitted thereby travels within said sensor body; and
   first and second photosensitive elements embedded within said sensor body, said first photosensitive element providing a response signal indicative of the level of interaction of said first indicator molecules with radiation interacting therewith and hence indicative of the presence or concentration of said first analyte, and said second photosensitive element providing a response signal indicative of the level of interaction of said second indicator molecules with radiation interacting therewith and hence indicative of the presence or concentration of said second analyte.

66. The sensor of claim 65, wherein the optical characteristic of said first indicator molecules which is responsive to changes in the concentration of said first analyte is the same as the optical characteristic of said second indicator molecules which is responsive to changes in the concentration of said second analyte.

67. An optical-based sensor for determining the presence or concentration of an analyte in a medium, said sensor comprising:
   an optically transmissive sensor body which functions as an optic wave guide, said sensor body having a surface;
   first and second indicator molecules disposed on the surface of said sensor body, said first indicator molecules having a first optical characteristic that is responsive to changes in the concentration of said analyte and said second indicator molecules having a second optical characteristic that is responsive to changes in the concentration of said analyte, said first and second optical characteristics being different from each other;
   a radiation source which emits radiation that interacts with said first indicator molecules in accordance with the first, analyte-responsive optical characteristic thereof and a radiation source which emits radiation that interacts with said second indicator molecules in accordance with the second, analyte-responsive optical characteristic thereof, said radiation source or sources being embedded within said sensor body such that radiation emitted thereby travels within said sensor body; and
   first and second photosensitive elements embedded within said sensor body, said first photosensitive element providing a response signal indicative of the level of interaction of said first indicator molecules with radiation interacting therewith and hence indicative of the presence or concentration of said analyte, and said second photosensitive element providing a response signal indicative of the level of interaction of said second indicator molecules with radiation interacting therewith and hence indicative of the presence or concentration of said analyte;
   whereby the presence or concentration of said analyte can be determined with a single sensor employing a plurality of transduction schema.

68. An optical-based sensor for determining the presence or concentration of an analyte in a medium, said medium having a first refractive index which varies as a function of the concentration of said analyte in said medium, said sensor comprising:
   an optically transmissive sensor body which functions as an optic wave guide, said sensor body having a second refractive index and a surface;
   a radiation source which emits radiation, said radiation source being embedded within said sensor body such that radiation emitted by said source travels within said sensor body; and
   a photosensitive element which is responsive to radiation emitted by said radiation source, said photosensitive element being embedded within said sensor body;
   wherein an amount of radiation emitted by said source passes out of said sensor body, the amount of radiation passing out of said sensor body varying as a function of the ratio of said first and second refractive indices and hence as a function of the concentration of said analyte in said medium, at least some of the radiation passing out of said sensor body being reflected internally within said sensor body before passing out of said sensor body; and
   wherein radiation not passing out of said sensor body is detected by said photosensitive element, at least some of the non-exiting radiation detected by said photosensitive element being reflected internally within said sensor body before striking said photosensitive element.

69. The sensor of claim 68, further comprising a power source which powers said radiation source to cause said radiation source to emit radiation, said power source being embedded within said sensor body.

70. The sensor of claim 69, wherein said power source comprises an inductor and said radiation source is caused to emit radiation by exposing the sensor to a field of electromagnetic radiation that is generated exterior to said sensor body.

71. The sensor of claim 68, further comprising a transmitter embedded within said sensor body, said transmitter transmitting from within said sensor body to the exterior of said sensor body a signal indicative of the concentration of the analyte.

72. The sensor of claim 71, wherein said transmitter comprises an inductor which generates a field of electromagnetic radiation that is detectable by a signal pickup device that is located exterior to said sensor body.

73. The sensor of claim 69, further comprising a transmitter embedded within said sensor body, said transmitter transmitting from within said sensor body to the exterior of said sensor body a signal indicative of the concentration of the analyte.

74. The sensor of claim 73, wherein said embedded power source powers both said radiation source and said transmitter.

75. The sensor of claim 68, wherein said sensor has an oblong, rounded shape whereby said sensor can be disposed within the body of a living human.

76. The sensor of claim 75, wherein said sensor has an overall length of approximately 500 microns to approximately 0.5 inch and a diameter of approximately 300 microns to approximately 0.3 inch.

77. The sensor of claim 68, further comprising a tissue/sensor interface layer disposed over the surface of said sensor body, said tissue/sensor interface layer being permeable to the analyte.

78. The sensor of claim 77, wherein said tissue/sensor interface layer retards formation of fibrotic encapsulation or scar tissue.

79. The sensor of claim 77, wherein said tissue/sensor interface layer comprises a sublayer which promotes tissue ingrowth therein.

80. The sensor of claim 79, wherein said tissue ingrowth comprises vascularization.

81. The sensor of claim 77, wherein said tissue/sensor interface layer comprises a molecular sieve sublayer which performs a molecular weight cutoff function.

82. The sensor of claim 77, wherein said tissue/sensor interface layer is selectively permeable so as to permit said analyte-containing medium to contact said surface while preventing cells or macromolecules from contacting said surface.

83. The sensor of claim 77, wherein said tissue/sensor interface layer is biocompatible.

84. The sensor of claim 68, further comprising a reflection enhancement layer disposed over a portion of the surface of said sensor body to enhance reflection within said sensor body of radiation emitted by said source.

85. The sensor of claim 68, wherein said radiation source comprises a light-emitting diode.

86. The sensor of claim 68, wherein said radiation source comprises a radioluminescent light source.

87. A method of determining the presence or concentration of an analyte in a medium, said method comprising the steps of disposing a sensor in the medium, said sensor comprising an optically transmissive sensor body which functions as an optic wave guide, said sensor body further comprising a source of radiation and a photosensitive element both embedded therein and indicator molecules disposed on a surface thereof, the indicator molecules fluorescing in response to radiation emitted by the source and the level of fluorescence varying with the presence or concentration of the analyte;

causing the source to emit radiation and internally illuminate the sensor body, radiation emitted by the source causing said indicator molecules to fluoresce and fluorescent light emitted by said indicator molecules passing into said sensor body;

detecting fluorescent light emitted by said indicator molecules and passing into said sensor body with said photosensitive element; and providing a response signal indicative of the level of fluorescent light detected by the photosensitive element and hence indicative of the presence or concentration of the analyte in the medium.

88. The method of claim 87, further comprising transmitting a signal indicative of the presence or concentration of analyte in the medium.

89. The method of claim 87, further comprising causing said source of radiation to emit radiation by means exterior to said sensor.

90. A method of determining the presence or concentration of an analyte in a medium, said method comprising the steps of disposing a sensor in the medium, said sensor comprising a sensor body with a source that emits radiation and a photosensitive element both embedded therein and indicator molecules disposed on a surface thereof, the indicator molecules absorbing at least some of the radiation emitted by the source and passing out of the sensor body and at least some of the radiation emitted by the source not being absorbed and being reflected back into the sensor body, the level of absorbance varying with the presence or concentration of the analyte;

causing the source to emit radiation and internally illuminate the sensor body, at least some of the radiation emitted by the source passing out of the sensor body and either being absorbed by the indicator molecules or being reflected back into the sensor body;

detecting radiation emitted by said source, passing out of said sensor body and not being absorbed by said indicator molecules, and passing back into said sensor body with said photosensitive element; and providing a response signal indicative of the level of radiation detected by the photosensitive element and hence indicative of the presence or concentration of the analyte in the medium.

91. The method of claim 90, further comprising transmitting a signal indicative of the presence or concentration of analyte in the medium.

92. The method of claim 90, further comprising causing said source of radiation to emit radiation by means exterior to said sensor.

93. A method of determining the presence or concentration of an analyte in vivo in a human subject, said method comprising the steps of inserting a sensor into the subject in a location of interest, said sensor comprising a fluorescence-based sensor which emits radiation and which has indicator molecules that fluoresce in response to said radiation, the level of fluorescence of said indicator molecules varying with the presence or concentration of said analyte, said sensor further comprising an optically transmissive sensor body which functions as an optic wave guide, said sensor further comprising a source a photosensitive element which senses fluorescent light emitted by said indicator molecules and which provides a response signal indicative of the level of fluorescence of said indicator molecules;

causing said sensor to emit radiation using means wholly exterior to the body of said subject; and detecting said signal indicative of the level of fluorescence of said indicator molecules using means wholly exterior to the body of said subject and determining the presence or concentration of the analyte therefrom.

94. A method of determining the presence or concentration of an analyte in vivo in a human subject, said method comprising the steps of inserting a sensor into the subject in a location of interest, said sensor comprising an absorbance-based sensor which emits radiation and which has indicator molecules that absorb at least some of said emitted radiation, the level of absorbance varying with the presence or concentration of said analyte, said sensor further comprising a photosensitive element which senses radiation not absorbed by said indicator molecules and which provides a response signal indicative of the level of sensed radiation;

causing said sensor to emit radiation using means wholly exterior to the body of said subject; and detecting said signal indicative of the level of sensed radiation using means wholly exterior to the body of said subject and determining the presence or concentration of the analyte therefrom.

95. A method of determining the presence or concentration of an analyte in a medium having a first refractive index, said method comprising the steps of disposing a sensor in said medium, said sensor comprising an embedded source of illumination and an embedded photosensitive element and having a second refractive index;

internally illuminating said sensor by means of said source of illumination, the level of internal illumination varying as a function of the first and second refractive indices;

measuring the level of internal illumination by means of said photosensitive element; and determining the presence or concentration of said analyte from the level of internal illumination.

* * * * *